(12) United States Patent
Mills

(10) Patent No.: US 9,936,913 B2
(45) Date of Patent: Apr. 10, 2018

(54) METHODS FOR CASCADING PURE ODORANTS TO THE NOSTRILS OF PATIENTS

(71) Applicant: INSPIRED TECHNOLOGIES, INC., LeSueur, MN (US)

(72) Inventor: Gregory B. Mills, Kansas City, KS (US)

(73) Assignee: Inspired Technologies, Inc., LeSueur, MN (US)

(*) Notice: Subject to any disclaimer, the term of this patent is extended or adjusted under 35 U.S.C. 154(b) by 0 days.

(21) Appl. No.: 15/094,327

(22) Filed: Apr. 8, 2016

(65) Prior Publication Data

US 2016/0249845 A1    Sep. 1, 2016

Related U.S. Application Data

(62) Division of application No. 14/795,606, filed on Jul. 9, 2015, now Pat. No. 9,717,454.
(Continued)

(51) Int. Cl.
*A61B 5/08* (2006.01)
*A61B 5/00* (2006.01)
(Continued)

(52) U.S. Cl.
CPC .......... *A61B 5/4011* (2013.01); *A61B 5/4088* (2013.01); *A61B 5/7246* (2013.01);
(Continued)

(58) Field of Classification Search
CPC combination set(s) only.
See application file for complete search history.

(56) References Cited

U.S. PATENT DOCUMENTS

| 3,885,550 A | 5/1975 | MacLeod |
| 4,265,248 A | 5/1981 | Chuiton et al. |

(Continued)

FOREIGN PATENT DOCUMENTS

| WO | WO2006/135368 | 12/2006 |
| WO | 2011/035284 | 3/2011 |

(Continued)

OTHER PUBLICATIONS

Müller, Gottfried, et al. "Reaction time prolongation in the early stage of presenile onset Alzheimer's disease." European archives of psychiatry and clinical neuroscience 241.1 (1991): 46-48 (Muller).*

(Continued)

*Primary Examiner* — Patricia Mallari
*Assistant Examiner* — Mitchell E Alter
(74) *Attorney, Agent, or Firm* — Barnes & Thornburg, LLP; Jeffrey R. Stone

(57) ABSTRACT

The present system is directed in various embodiments to devices, systems and methods for detection, evaluation and/or monitoring olfactory dysfunction by measuring and determining the patient's olfactory detection threshold for the left and the right nostril. More specifically, the present invention relates to devices, systems and methods for detecting an asymmetric differential in a patient's olfactory detection threshold (left vs right nostril) which, when present, may be used as a tool to screen, detect, diagnose and/or monitor relative olfactory deterioration resulting from Alzheimer's disease. A preferred embodiment comprises cascading aromas by serially administering more than one pure odorant to the patient's nostrils, left vs right, with measurement of the time, or numbers of breaths, required to cognitively notice the pure odorants' presence.

22 Claims, 14 Drawing Sheets

Related U.S. Application Data

(60) Provisional application No. 62/023,352, filed on Jul. 11, 2014, provisional application No. 62/108,239, filed on Jan. 27, 2015.

(51) Int. Cl.
*A61M 15/08* (2006.01)
*A61M 21/00* (2006.01)
*A61M 15/00* (2006.01)

(52) U.S. Cl.
CPC ......... *A61B 5/7282* (2013.01); *A61M 15/08* (2013.01); *A61M 15/0015* (2014.02); *A61M 15/0016* (2014.02); *A61M 15/0043* (2014.02); *A61M 15/0048* (2014.02); *A61M 2021/0016* (2013.01); *A61M 2205/583* (2013.01)

(56) References Cited

U.S. PATENT DOCUMENTS

| | | | |
|---|---|---|---|
| 4,934,386 | A | 6/1990 | Walker et al. |
| 5,565,548 | A | 10/1996 | Neurath et al. |
| 6,325,475 | B1 | 12/2001 | Hayes et al. |
| 6,467,332 | B1 | 10/2002 | Bertschi et al. |
| 6,957,038 | B1 | 10/2005 | Gartner et al. |
| 7,007,694 | B2 | 3/2006 | Aylsworth et al. |
| 8,429,950 | B2 | 4/2013 | Wright |
| 8,469,293 | B2 | 6/2013 | Doty et al. |
| 8,826,723 | B2 | 9/2014 | Henry |
| 2003/0033852 | A1 | 2/2003 | McGinley |
| 2005/0046049 | A1 | 3/2005 | Watkins et al. |
| 2005/0192482 | A1 | 9/2005 | Carpenter et al. |
| 2007/0062255 | A1 | 3/2007 | Talton |
| 2007/0277824 | A1 | 12/2007 | Aylsworth et al. |
| 2008/0223953 | A1 | 9/2008 | Tomono et al. |
| 2009/0049988 | A1* | 2/2009 | Meindl ............... B01D 53/228 95/285 |
| 2010/0056946 | A1 | 3/2010 | Holmes |
| 2011/0030450 | A1 | 2/2011 | Wright |
| 2011/0253800 | A1 | 10/2011 | Doty et al. |
| 2012/0078065 | A1 | 3/2012 | De Lemos et al. |
| 2012/0184828 | A1 | 7/2012 | Lundstrom et al. |
| 2013/0012828 | A1 | 1/2013 | Aylsworth |
| 2013/0239657 | A1 | 9/2013 | Henry |
| 2014/0316485 | A1 | 10/2014 | Ackermann et al. |

FOREIGN PATENT DOCUMENTS

| | | | |
|---|---|---|---|
| WO | WO 2013/150446 | * | 10/2013 |
| WO | WO2013/150446 | | 10/2013 |

OTHER PUBLICATIONS

Martzke, Jeffrey S., Lili C. Kopala, and Kimberley P. Good. "Olfactory dysfunction in neuropsychiatric disorders: review and methodological considerations" Biological psychiatry 42.8 (1997): 721-732 (Martzke).*

International Preliminary Report on Patentability, dated Apr. 26, 2016 for International PCt Appication No. PCT/US2014/061574, filed Oct. 21, 2014.

European Extended Search Report from related EP application No. 14855407.4, dated May 2, 2017.

Monique A.M. Smeets et al.: "Seeing occupational exposure limits in humans: contributions from the field of experimental psychology", International Archives of Occupational and Environmental Health, Springer, Berlin, DE, vol. 79, No. 4, May 1, 2006 (May 1, 2006), pp. 299-307, XP019343393, ISSN: 1432-1246, DOI: 10.1007/S00420-005-0053-8, abstract, p. 300, col. 2—p. 303, col. 2.

* cited by examiner

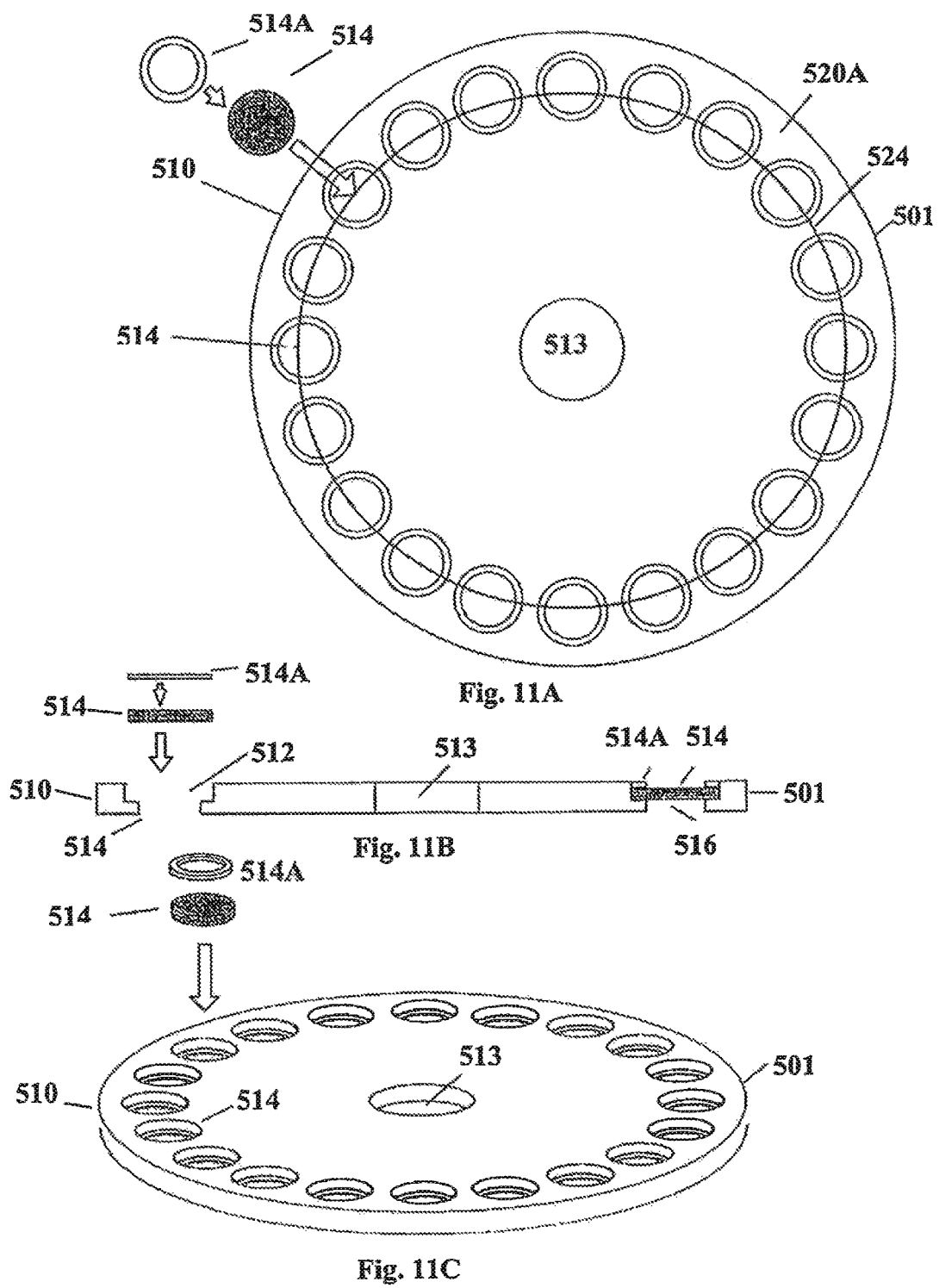

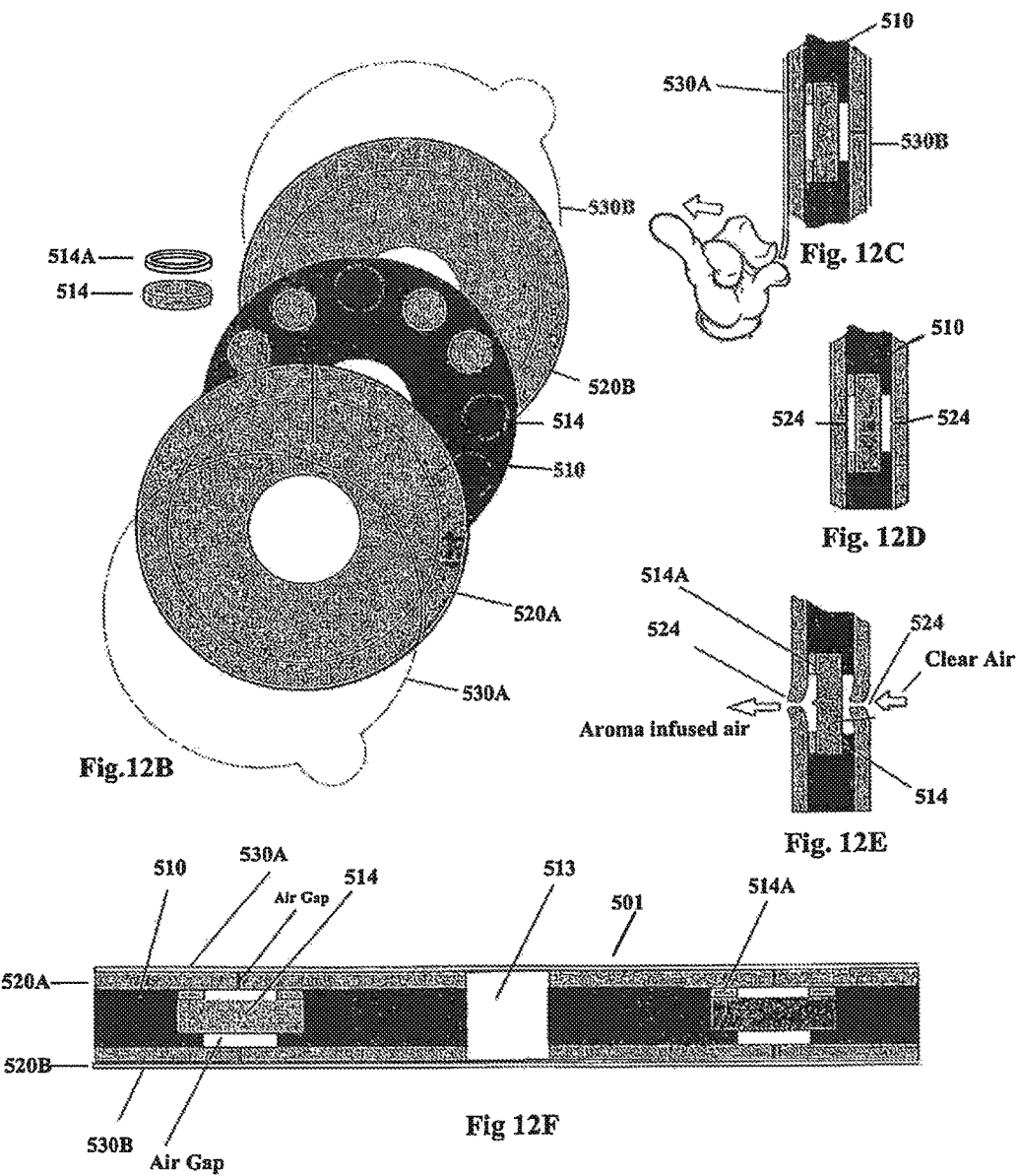

METHODS FOR CASCADING PURE ODORANTS TO THE NOSTRILS OF PATIENTS

CROSS-REFERENCE TO RELATED APPLICATIONS

This application is a divisional of application Ser. No. 14/795,606, entitled "Devices, Systems and Methods for Detecting a Bilateral Differential in Olfactory Detection Threshold for Pure Odorants", and claims priority to App. Ser. No. 62/023,352, entitled "Improved Devices, Systems & Methods For Quickly Detecting Bilateral Differentials In Olfactory Threshold, Presenting A Cascading Plurality Of Pure Aromas", filed Jul. 11, 2014, and to App. Ser. No. 62/108,239, entitled "Method For Screening Bilateral Differentials In Olfactory Aroma Detection And Confirming Alzheimer's Disease Through Retinal Plaque Deposits", filed Jan. 27, 2015, the entire contents of each of which are hereby incorporated by reference.

FIELD OF THE INVENTION

The present invention generally relates to devices, systems and methods for determining relative bilateral olfactory detection thresholds. More specifically, the present invention relates to devices, systems and methods for detecting an asymmetrical differential in a patient's olfactory detection threshold as measured at the left and right nostrils and that, when present, a significant asymmetrical differential may indicate olfactory deterioration and may, therefore, be used as a screening tool for Alzheimer's disease.

DESCRIPTION OF THE RELATED ART

Aroma testing in the past has been generally related to the overall aroma detection of a person, commonly by naming a particular odor, without particular interest in comparing the relative smelling ability of their nostrils or the type of aromas they could and could not smell. Published articles document that a relatively poor sense of smell in the left nostril, or sensitivity, as compared to the sensitivity of the right nostril may be indicative of early brain damage due to neurological disease. See, e.g., Murphy, et al., "Left hippocampal volume loss in Alzheimer's disease is reflected in performance on odor identification: A structural MRI Study", Journal of the International Neuropsychological Society, Vol. 9, No. 3, pp 459-471 (2003). This is the case in Alzheimer's Disease (hereinafter AD), but is of clinical significance in the early detection of AD, however, only if the aroma used in the test is a pure aroma for reasons that are discussed further infra.

It is estimated that up to 40% of the elderly have undiagnosed early on-set Alzheimer's disease, but have not been diagnosed as their dementia is quite mild at this point. Under these circumstances, an early diagnostic tool, e.g., before clinically detectable dementia is observed or diagnosed, is critical to enable therapies to be initiated to slow, or perhaps even reverse, the progression of the disease.

Improved diagnostic screening methods useful in living people include: various blood tests, many seeking to identify specific lipids seen only in advanced AD patient's blood. Aroma detection screens, genetic markets for AD, radiological procedures, written cognitive tests on paper or on computer devices have all been improved with varying levels of efficacy. Amyloid Plaque deposit detection in eye tissue and other screening methods, seek to detect telltale precursors of AD before significant damage is done to the brain.

Another screening methodology takes advantage of the notable deficit of smelling ability in the left nostril as compared to the smelling ability of the right nostril to detect a pure aroma, appears according to previous medical research, to be indicative of early neurological degeneration of the olfactory nerve, specifically as seen in the early onset of AD.

The olfactory nerve is found on the left side of the brain and is not reversed bilaterally as many brain functions are, such as eye sight. Research, including data from autopsies, indicates that degeneration of the olfactory nerve occurs gradually and begins very early in the disease development of AD. Such deterioration may begin years before substantial dementia becomes notable. Thus currently a diagnosis of AD becomes confirmed by existing testing procedures that are generally focused on observation, detection and/or diagnosis of actual dementia. This is problematic in the detection of AD because, inter alga, dementia presents in other non-AD diseases, conditions and/or disorders. Moreover, at such late disease stages, AD is generally not amenable to treatment. Consequently, screening and diagnosis at the earliest stage possible is critical.

The "pure odorant detection threshold" is the point at which an increasing concentration of pure odorant molecules saturate the olfactory nerve to the extent that a cognitive reaction first takes place, where the patient recognizes they are smelling something, but haven't yet cognitively been able to identify the odor by name. There is a latent period between introduction of the pure odorant molecules into the patient's nostrils and when the pure odorant detection threshold is reached. Measurement of this latent period can be of clinical utility. In the case of early onset AD, the latency in the left nostril may be greater than that of the right nostril, providing very early clinical indication of the presence of AD. The olfactory function differential favoring the right side disappears in well advanced AD, as the entire brain deteriorates the right side catches up in deterioration so that both sides are profoundly impacted.

The "pure odorant identification threshold" represents a slightly longer latent period than the "pure odorant detection threshold" as it is the point at which the patient is able to cognitively process the odor and then actually identify the odorant by name.

A general process for measuring the left nostril latent period and related bilaterally asymmetrical olfactory nerve deterioration is recently described in the "peanut butter aroma test" reported by Jennifer Stamps at the University of Florida. The Stamps method uses a simple but effective protocol where a common centimeter ruler is held up to the nose of the test subject. The subject is instructed to close their eyes and cover one nostril as a spoonful of peanut butter, a pure odorant as defined infra, is slowly moved towards their nose. The clinical technician notes the estimated distance in centimeters between the aroma source and the nostril of the test subject at the point the first aroma detection threshold is noted by the subject. Two testing events might result in the following exemplary pure odorant olfactory threshold values: 12 centimeters on the left nostril and 21 centimeters on the right nostril.

Both the left and right nostrils were tested several times under the Stamps methodology and in random order with a 90-second "reset period" between trials to clear the olfactory gland of the odorant. The relative smelling ability of the two nostrils were then compared using known statistical techniques. Effectively, the Stamps method amounts to an indirect measurement of concentration required for cognitive notice of peanut butter aroma presented to a nostril, based upon reducing the distance between the aroma source and the nostril. Stamps uses a single pure odorant with an endpoint identified as the distance from aroma source to the nostril at the transition point where no scent is detected to a scent cognitively noticed. Stamps, therefore, uses the "pure odorant identification threshold" as an endpoint.

"Pure odorant", also referred to equivalently as "pure aroma" or "aroma" herein, is defined as substances including molecules and/or compounds which principally stimulate the olfactory cell receptors associated with the first cranial nerve and that do not trigger or excite the trigeminal nerve associated with the fifth cranial nerve.

Thus, the use of a "pure odorant" for aroma testing is critical in the context of, inter alia, detection of relative deterioration of smelling sensitivity in the left nostril compared with the right nostril.

However, the Stamps method presents some obvious issues rendering it generally unacceptable for repeatable and robust clinical results. Namely, Stamps fails to consider patients' nasal structural issues which may contribute to low airflow and may contribute to poor threshold detection ability in a given nostril. In addition, Stamps fails to consider the general airflow within the testing environment and how that may impact the test results. It is clear that commercialization of the methodology requires a well-defined clinical protocol and more accurate and robust devices and testing methods. Stamps also requires an at least 90 second reset period between screening events to allow the subject to prepare for the next aroma presentation. This "reset" period wastes valuable time and variations from person-to-person may require longer than the prescribed 90 second period. Stamps also fails to use the "pure odorant detection threshold", opting instead for the later-in-time "pure odorant identification threshold". Finally, Stamps fails to recognize the advantage of "olfactory sensory dissonance" defined as a phenomenon whereby an aroma having been noticed by a subject, that declines in perceptive concentration as it is replaced by an increasing concentration of a second aroma tends to crisply shift full cognitive notice to the second aroma and the first aroma is then quickly forgotten.

Nonetheless, the Stamps test and other related previously published research papers support the conclusion that an inability to detect a single pure aroma or odorant relatively equally in both nostrils, especially when the deficit is more notable in the left nostril, may indicate olfactory nerve damage and, therefore, indirectly the early onset of AD.

Applicant has developed several solutions to the problem of bilateral screening as further described in U.S. patent application Ser. No. 14/282,622, entitled DEVICES, SYSTEMS AND METHODS FOR DETECTING A BILATERAL DIFFERENTIAL IN OLFACTORY THRESHOLD FOR PURE ODORANTS, the entire contents of which are hereby incorporated by reference.

A chain of scientifically based facts are behind aroma detection screening to detect damage to the olfactory nerve, also referred to as the first cranial nerve:

1. There are a number of "pure odorants" that can only be detected by the olfactory nerve and not the trigeminal system.

2. Autopsy results indicate that the earliest indications of AD occur near the olfactory nerve on the left side of the brain.

3. The olfactory nerve is anatomically located behind the left nostril.

4. The loss of the sense of smell for pure aromas occurs first on the left side of the brain proximate the olfactory nerve in the AD development process.

5. The right nostril can act as a control to find a relative strength of the nostrils as a ratio.

6. An increasing concentration of pure aroma triggers a cognitive notice most people are aware of and can cognitively react to.

7. Due to the phenomenon of olfactory sensory dissonance an aroma having been noticed by a subject, that declines in apparent concentration as it is replaced by an increasing concentration of a second aroma that tends to crisply shift full cognitive notice to the second aroma and the first aroma is then quickly forgotten.

Bilateral aroma testing may, but need not, include comparison using a known absolute concentration of aroma for scientific validation. Instead, a preferred embodiment may comprise a relative comparison, in finding which nostril is sensitivity is greater or weaker. Some variation is normal, but a profound difference is likely significant baring identifiable medical reasons for the loss of symmetrical sensitivity.

Thus, the "relative sensitivity" of the two nostrils is a preferred variable being sought for olfactory damage assessment, rather than "absolute sensitivity" using embodiments of the present invention.

Some people have been exposed to industrial chemicals or paints that have damaged their sense of smell. However such chemicals likely impacted both nostrils relatively equally since such damaging chemical exposure was equal. In addition, research indicates that a relative equal loss of the sense of smell for pure aromas on both sides, as compared to a normal detection level, might be indicative of other neurological diseases, such as Parkinson's disease which impacts both nostrils equally.

Surgery or a serious brain infection or serious head trauma for example, might render one nostril's sensitivity damaged or completely unable to function without presenting an accurate indication of AD linked olfactory damage. Some people are genetically handicapped in their sense of smell for pure aromas lacking any known trauma.

A deviated septum might reduce air flow on the affected side which might skew results slightly in favor of the non-impacted nostril. Actual field testing data indicate that the effect of a restricted airway is not as much an issue as anticipated, but the condition still needs to be considered. Congestion and other reasons for temporary odor sensitivity impaction need to be eliminated or considered as a disqualification for the aroma screen in severe cases. An alternative AD screen should then be used, such as the cur cumin retinal study.

Generally however, according to studies, a deteriorated sense of pure aroma or odorant detection in the left nostril is neurologically significant when the subject is screened. Such pure aroma screens indirectly assess the condition of the olfactory nerve by presenting pure aroma in a controlled way, such that the concentration and sort of aroma is manipulated by the testing personnel and only one nostril at a time is served aroma. The relative strength of the nostrils is the metric of interest in detecting AD.

All known early onset AD screening methods lack a uniform staging system for measuring and communicating the relative state of a patient's AD development. A uniform disease risk staging system needs to be established similar to the cancer staging of 1-4. Various cancers have well defined staging methods. Different cancers have different criteria for staging wherein stage 1 is less serious than stage 3, for example.

A common diagnostic scoring metric for AD would advance medical research studies by, inter alia, universally defining AD developmental stages.

Further, a risk factor scoring method that takes the totality of a patient's medical history and the various AD screening methods into account to render an AD "risk factor" is also badly needed. These two metrics would sort people into those with a low risk factor, a high risk factor without AD and an actual AD stage.

A staging metric would also help Doctors diagnose AD earlier and with a greater level of confidence than has been previously possible with living patients. AD diagnosis at an earlier point in disease development will benefit the patient by facilitating more efficacious early AD treatment, hopefully before significant brain damage occurs.

An AD scaling method would also provide a pool of qualified candidates at various stages of the disease for clinical trials of potentially efficacious drugs. Having access to a large pool of known early onset AD patients would certainly advance clinical studies dramatically.

However, all known AD screening methods have various unrelated Alzheimer's Disease risk scoring systems, or none at all. Therefore, these screens fail to offer doctors an overall AD risk factor in the context of the full medical history for that particular patient. A meaningful and fundamentally helpful report for Doctors to use in deciphering and communicating the actual risk of a certain patient developing AD in the future is sorely needed.

An efficacious AD risk factor report for doctors enables the rendering of a firm diagnosis of Alzheimer's disease based upon a clear medical standard that can be universally understood and communicated. Typically, AD cases are not firmly diagnosed until all alternative causes of dementia that is clearly presented, have all been ruled out.

An Alzheimer's disease risk factor scoring system that is able to encompass all the various relevant medical history issues as well as interpret efficacious AD screens, that have been performed on the living, is needed to provide medical practitioners diagnostic information in a useable form. The staging method needs to look at the overall data for a particular patient to put all the data into a proper context. An accepted system for staging Alzheimer's disease is currently lacking due to the previous difficulty in even confirming that a particular patient actually has the disease at all, prior to the autopsy.

Amyloid plaque deposits and protein tangles are the microscopic evidence sought to confirm AD in diseased patients in autopsy. Amyloid plaque deposits also appear in the retina and iris and are visible with various stains that jump the blood brain barrier and are fluoresced by specific spectrums of light. Thus, is possible to observe plaque deposits in the eye of a living person non-invasively and deduce from what is seen in the eye what would be apparent if the brain cavity were opened.

A patient suffering some dementia (which easily diagnosed with cognitive testing), who has a notable deterioration of sensitivity to pure aroma on the left side, without a known medical reason, who also has had a baseline retinal photograph examined by an ophthalmologist and then had a cur cumin plaque detection study done which identified amyloid plaque on their retina, almost certain has AD. The relative amount of amyloid plaque seen is directly proportional to the stage of AD.

Other neurologic screening methods, e.g., the University of Pennsylvania's "UPSIT" aroma sensitivity screen claim to identify olfactory and scent memory problems, but fails to differentiate between the two nostrils, and therefore fails to identify any odorant threshold differential between the nostrils. Further, the UPSIT scratch and sniff scent identification test fails by design to differentiate between pure aromas that are perceived exclusively by the olfactory organ or harsher smell by the trigmenial system. Mixing Lemon and Gasoline in one test is certainly behind the times in olfactory research.

In our research we discovered that the fidelity of the scratch and sniff samples is amazingly poor. The ink used for scratch and sniff printing requires that odorants used be completely free of water, which requires chemical approximations of scents rather than actual essential oils or the like. The UPSIT also uses combinations of aromas that certainly are not universally familiar to people. Bubble Gum for example comes in many flavors which makes it tricky to pick the aroma the testers expected.

In a small clinical trial performed by Inspired Technology the scratch and sniff scent for Orange was thought to be Bubble Gum by 7 participants, Cheddar Cheese by 1 with 2 not hazarding a guess with no one of the 10 recognizing Orange. Cheddar Cheese on the other hand was thought by 8 out of 10 to be paint thinner with no one guessing Cheddar Cheese. Lemon was thought to be Motor Oil by 7 out of 10 participants with one hazarding Rose.

The UPSIT is also culturally biased as familiar scents in the USA are not so familiar in India, for example. Thus, a test media that uses actual essential oils, with a device that differentiates the nostrils and has a way to offer a plurality of aroma test sets at little expense.

Consequently, the UPSIT data cannot be used as an accurate screening mechanism for at least AD.

Thus, a need exists in the art generally for an inexpensive, easy to use, accurate and repeatable clinically significant device, system and method for detecting an asymmetric (left vs right) differential in the olfactory detection threshold of a patient, preferably without a required "reset" period. Such devices, systems and methods may be used to assist a physician in screening and/or detecting AD and/or risk of developing AD, before the clinical presentation of dementia occurs.

The present invention addresses these, among other, needs.

BRIEF SUMMARY OF THE INVENTION

The present system is directed in various embodiments to devices, systems and methods for detection, evaluation and/or monitoring olfactory dysfunction by measuring and determining the patient's olfactory detection threshold for the left and the right nostril. More specifically, the present invention relates to devices, systems and methods for detecting an asymmetric differential in a patient's olfactory detection threshold (left vs right nostril) which, when present, may be used as a tool to screen, detect, diagnose and/or monitor relative olfactory deterioration resulting from Alzheimer's disease. A preferred embodiment comprises cascading aromas by serially administering more than one pure odorant to the patient's nostrils, left vs right, with measurement of the time, or numbers of breaths, required to cognitively notice the pure odorants' presence and without a reset or clearing period between presentation of successive odorants. The device disclosed is also useful for scent identification tests and scent concentration tests as a testing platform.

BRIEF DESCRIPTION OF THE DRAWINGS

FIG. 6A illustrates a ratcheted gear advancer mechanism.

FIG. 6B illustrates a wound spring gear advancer mechanism.

FIG. 9A illustrates a perspective and partial exploded view of one embodiment of the present invention.

FIG. 9C illustrates a partial cutaway front view of the embodiment of FIGS. 9A and 9B.

FIG. 11A illustrates a front view of one embodiment of a loaded pure odorant or pure odorant cartridge.

FIG. 11B illustrates a side view of the embodiment of FIG. 11A illustrating the loading of an odorant or pure odorant into the cartridge.

FIG. 11C illustrates a perspective view of one embodiment of the present invention.

FIG. 12B illustrates an exploded view of one embodiment of odorant or pure odorant cartridge.

FIG. 12C illustrates a side cutaway view of one embodiment of odorant or pure odorant cartridge.

FIG. 12D illustrates a side cutaway view of one embodiment of odorant or pure odorant cartridge.

FIG. 12E illustrates a side cutaway view of one embodiment of odorant or pure odorant cartridge.

FIG. 12F illustrates a side view of one embodiment of odorant or pure odorant cartridge.

DETAILED DESCRIPTION

Figure 1:
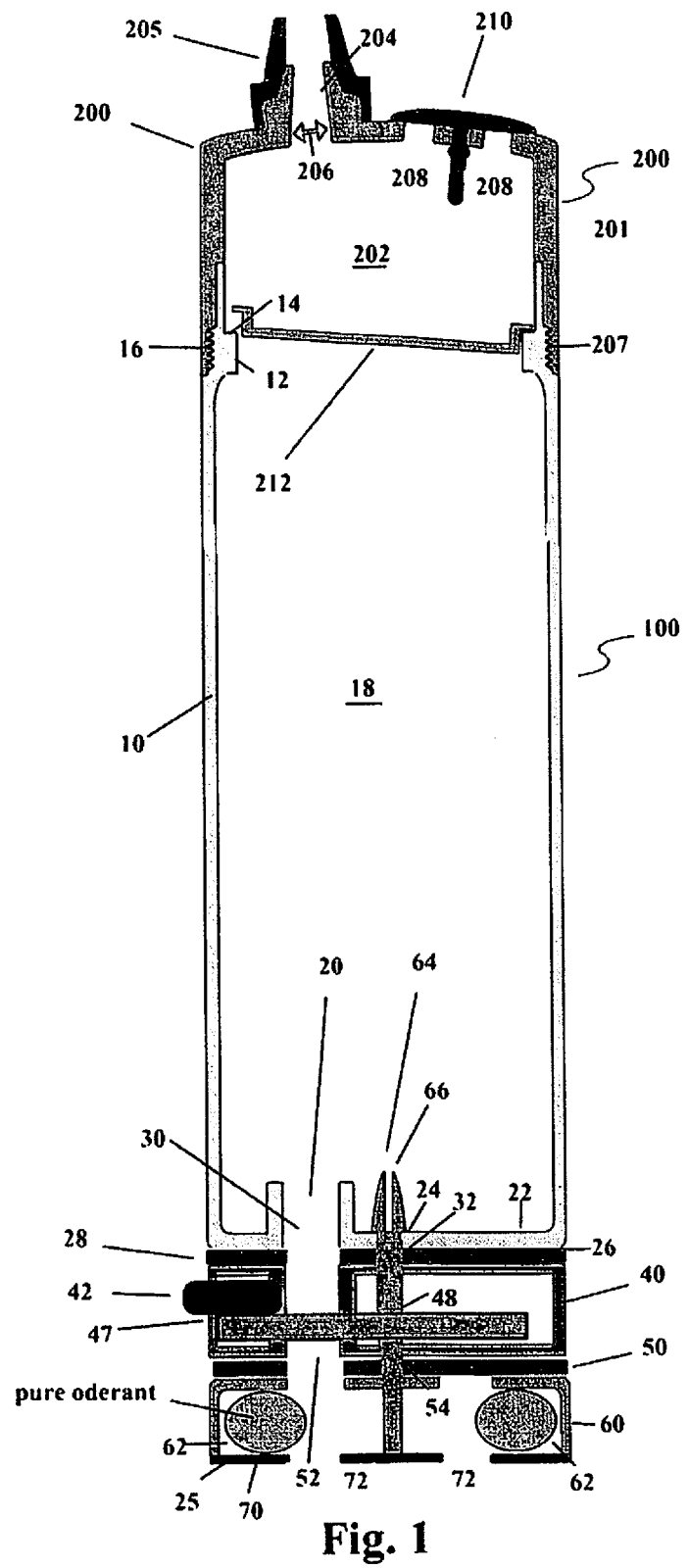
FIG. 1 illustrates a cross-sectional front view of one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

The present system is directed in various embodiments to devices, systems and methods for detection, evaluation and/or monitoring olfactory dysfunction by measuring and determining the patient's olfactory detection threshold for the left and the right nostril. More specifically, the present invention relates to devices, systems and methods for detecting an asymmetric differential in a patient's relative olfactory detection threshold (left vs right nostril) which, when present, may be used as a device to detect, diagnose and/or monitor olfactory deterioration resulting from Alzheimer's disease.

Definitions

As used herein, "symmetric" or "symmetrical" means that there is not a significant differential in the subject patient's ability to detect and/or identify odors between odors administered and/or inhaled into the patient's left nostril vs. the patient's right nostril as measured by the olfactory threshold determined for each nostril.

As used herein, "asymmetric" or "asymmetrical" means that there is a significant asymmetry or differential in the subject patient's ability to detect and/or identify odors between odors administered and/or inhaled into the patient's left nostril vs. the patient's right nostril as measured by the olfactory threshold determined for each nostril.

"Hyperosmia" is defined as increased olfactory acuity, or a decreased threshold for detecting odors, and may be symmetric or asymmetric as those terms are defined herein. Various embodiments of the present invention may detect and/or monitor hyperosmia or treatments therefore.

"Hypoosmia is defined as diminished or decreased olfactory acuity, or an increased threshold for detecting odors, and may be symmetric or asymmetric as those terms are defined herein. Various embodiments of the present invention may detect and/or monitor hypoosmia or treatments therefore.

"Anosmia" is defined as the inability to recognize odors and may be symmetric or asymmetric as those terms are defined herein. Various embodiments of the present invention may detect and/or monitor anosmia or treatments therefore.

"Dysosmia" is defined as the abnormal sense of smell and may be symmetric or asymmetric as those terms are defined herein. Various embodiments of the present invention may detect and/or monitor dysosmia or treatments therefore.

"Olfactory dysfunction" is defined herein as a patient with a disorder and/or condition with one or more of the following: hyperosmia, hypoosmia, anosmia, and dysosmia. The olfactory dysfunction may be symmetric or asymmetric as those terms are defined herein.

"Pure odorant", also referred to equivalently as "pure aroma" is defined as substances including molecules and/or compounds which principally stimulate the olfactory cell receptors associated with the olfactory nerve, aka the first cranial nerve, and that do not trigger or excite the trigeminal nerve associated with the fifth cranial nerve. A non-exhaustive and categorized listing of pure odorants follows:

The pure odorant Spice family comprises:
Cinnamon;
Clove;
Vanilla;
Nutmeg; and
Allspice.
The pure odorant Food family comprises:
Peanut/Peanut Butter;
Coffee;
Cocoa;
Apple;
Almond (bitter); and
Strawberry.
The pure odorant Herbal family comprises:
Peppermint;
Spearmint;
Wintergreen;
Allspice;
Parsley;
Sage;
Turmeric;
Thyme;
Basil;
Dill weed;
Caraway;
Anise;
Fennel;
Mace;
Palmarosa; and
Patchouli.
The pure odorant Floral family comprises:
Rose;
Lemongrass;
Rosemary;
Lavender;
Lilac;
Violet; and
Origanum.
The pure odorant Citrus family comprises:
Orange;
Tangerine;
Lemon;
Lime;
Mandarin;
Grapefruit;
Bergamot and
Petitgrain.
The pure odorant Wood and Resin based family comprises:
Eucalyptus;
Juniper berry;
Pine;
Tea tree;
Spruce;
Ho wood;
Cypress;
Cedar;
Birch;
Fir;
Cajeput;
Camphor;
Cassia;
Citronella;
Clary;
Copaiba;
Elemi;
Hydacheim;
Litsea; and
Niaouli.

"Pure odorant detection threshold" is defined as the point at which the concentration of pure odorant molecules saturate the olfactory nerve to the extent that a cognitive reaction first takes place. At this point, the subject patient is able to express that he or she is smelling something, but not necessarily able yet to identify the aroma by name. The pure odorant detection threshold may be found to be asymmetrical, i.e., significantly different as between the nostrils, indicating olfactory dysfunction. Alternatively, the pure odorant detection threshold may be found to be symmetrical between the tested nostrils.

"Pure odorant identification threshold" represents a slightly longer latent period than the "pure odorant detection threshold" as it is defined as the point at which the patient is able to actually identify the pure odorant by name, indicating that cognitive processing has occurred.

"Odorant" is defined herein as a compound that does trigger the trigeminal nerve.

"Odorant detection threshold" is defined as the point at which the concentration of odorant molecules saturate the olfactory nerve to the extent that a cognitive reaction first takes place. At this point, the subject patient is able to express that he or she is smelling something, without necessarily identifying the aroma. The odorant detection threshold may be found to be asymmetrical, i.e., significantly different as between the nostrils, indicating olfactory dysfunction. Alternatively, the odorant detection threshold may be found to be symmetrical between the tested nostrils.

"Odorant identification threshold" is defined herein as the point at which the patient is able to actually identify the odorant by name, indicating that cognitive processing has occurred. The odorant identification threshold may or may not be symmetrical between the nostrils.

"Effective amount" of the odorant or pure odorant is defined as the amount of pure odorant required to infuse the aroma airway passage during operation of the various devices, systems and methods of the present invention sufficiently to enable a patient to smell the pure odorant, i.e., when saturation of the olfactory nerve is sufficient to enable the reaching of the pure odorant detection threshold for the patient and nostril being tested.

"Clear air", also referred to as pure air, is defined as air that does not comprise the odorant used in the inventive embodiments of the present invention. Preferably, clear air comprises air that is substantially uncontaminated by any odorant, including pure odorants. Clear air may comprise ambient air, i.e., atmospheric air, either filtered or unfiltered, or air that is provided from a clear air source such as an air tank or nebulizer and/or from a mechanized powered air pump as is well known in the art.

"Reset Period" is defined as a rest time between presentations or introductions of odorants or pure odorants, known reset periods are in the range of 90 seconds.

Aroma detection testing is done for many reasons and in a number of ways to accomplish various purposes, including diagnostic medical tests. Odor identification for example, comprise a common olfactory function that is tested. Numerous odor identification devices and methods have been developed to screen for what might be called a "scent memory function". This sort of testing metric might be called "Tell me what you smell?" This corresponds to the presently defined "pure odorant identification threshold". This endpoint for testing has several serious problems, not the least of which is the required inclusion of cognitive identification of the aroma or odor presented.

Pure aroma olfactory detection threshold response time is of particular clinical interest, especially when done bilaterally. In other words, the same aroma sensing test is preformed separately on each nostril and the test results compared, left nostril vs right nostril. This is done without aroma identification even being required. Perhaps the metric could be called, "Tell me when you smell something."

A Baseline of Pure Air Vs Aroma Laden Air as a Testing Metric

Concentrations of a single aroma may be gradually increased in unscented air until cognitive awareness of the presence of the aroma is noted. The distance between the aroma source (a spoonful of peanut butter) and the nostril may be measured as a diagnostic metric upon the patient first noting the peanut butter aroma. "With your eyes closed and one nostril covered, tell me when you first smell the aroma, which I am slowly moving closer to your nose along the ruler".

Alternatively, the time interval can be measured in seconds between aroma presentation to the subject, who is inhaling through an aroma presentation device, until the time interval ends upon cognitive notice that an aroma was noted. "Tell me the second you smell the aroma". Time in seconds is the metric recorded, indirectly measuring the level of odor concentration of aroma required to trigger cognitive notice.

Similarly, the number of breaths taken from the point of first introduction or presentation of the aroma until cognitive notice by the subject is a valid metric indirectly scaling the aroma detection ability of the nostrils.

The aroma presentation device might emit an audible tone when the exhalation portion of the breathing cycle is taking place to help the testing personnel note the precise number of breaths taken during the presentation of the aromas, in this mode of testing. The number of breaths taken before cognitive notice of the aroma is also an indirect measurement of the concentration of aroma required to get cognitive notice, which measures olfactory function.

Finally, the metric of the absolute concentration of an increasing aroma level required for cognitive notice, (as measured by an electronic nose module with a digital readout), may be used in the pure air vs aroma air laden air model of bilateral olfactory testing. A plurality of sample of one pure aroma with a spectrum of dilutions might be presented with the smallest concentration detectable ramped up in small steps to a stronger concentration might be used with first one nostril and then the other to detect the weaker nostril.

The metric of single aroma might be considered comparing no smell in the air as a baseline compared to a slowly increasing concentration of pure aroma infused in clear room and recording some definable metric used for clinical comparison between the nostrils. All of these metrics indirectly score olfactory function for detection of pure aromas.

Controlling the presentation of aroma may be done in a number of ways, each with advantages and disadvantages which may be mitigated with proper protocols and advanced device design.

1. Testing bilateral olfactory acuity using a contained and controlled aroma source has the advantage of removing the skewing effect of the movement of room air. A variable control completely lacking in the distance to the nose method mentioned above. The aroma is introduced directly into the nostril of the person being tested with this method.

The aroma concentration is thus more consistent, controllable and the results more repeatable when the aroma is contained and directed into a nostril. Containing the aroma source and directing it into the nostril of the test subject allows a precisely measured presentation of aroma containing air, with the cognitive threshold sensitivity scored or quantified numerically in a number of ways. A reset period between testing events must also be allowed using any method that presents only one aroma since the comparison is no aroma vs aroma detected.

Containing aroma within a device presents potential issues with "mechanical latency". Aroma molecules tend to stick to certain materials more than on others. Any amount of latent aroma tends to confuse the subject of the screening, but it is possible to contain aroma without contaminating the device and render the screen inaccurate, as will be explained below.

2. The time in seconds between control air with no aroma present and a controlled increasing concentration of aroma becoming detectable is a useful metric for bilateral aroma sensitivity testing. When the test is done sequentially for both nostrils using the same device and same aroma source, the ratio of aroma sensitivity may be accurately tested by using time. The nostril that takes longer or requires a higher level of aroma to recognize the presence of the aroma is the weaker nostril. A reset period between screening events is still required if only one aroma is used.

3. The number of breaths it takes to recognize the presence of an aroma being presented beginning with breathing controlled air with no aroma present is a potentially useful testing metric that has the advantage of not even requiring a clock. A reset period between screening events is required since only one aroma is being used.

4. Cascading a series of pure aromas presented to a single nostril where the number of seconds or the number of breaths required to cognitively realize that an alternative pure aroma is presented generates meaningful data and can quantitatively rate the relative performance of the two nostrils. Using at least two pure odorants presented one after another makes a reset period between events unnecessary, which will save time administering the screen using this method.

Of all methods of aroma screening noted, the lack of a reset period is particularly significant. When a plurality of aromas are presented sequentially, the olfactory nerve and brain can only concentrate on one aroma at a time due to the phenomena of "olfactory nerve dissonance". The function works to avoid our senses overwhelming us. We can ignore what we have sensed previously to be quickly ready to focus on something new . . . and in prehistoric times, potentially dangerous.

It is a known phenomenon of the olfactory nerve that the human sense of smell is elegantly sequential in its ability to note a specific new odor and "forget" or ignore the previous aroma. This effect is called odor dissonance. This feature of olfactory function is of significant utility in bilateral pure aroma testing using a cascading method. This test might be described as "tell me when the aroma you smell has changed to a new aroma" not "tell when you can smell one aroma" or "can you name the aroma"?

When an aroma is presented and a second aroma becomes notable, the brain "forgets" the previous aroma and concentrates on the fresh aroma. Cascading aromas thus takes advantage of that primitive neurological effect to evade the reset period required in single aroma screening methods.

7. Odor identification tests generally contain a plurality of familiar aromas which may be cognitively challenging to demented patients who struggle to find the word in their failing memory that describes an aroma that seems familiar to them, but is hard to place its name. Simply asking someone to note when the present aroma changes to a fresh aroma, as in the cascading screen, without being required to name the aroma is less taxing cognitively.

Most participants using a screen for AD will be older and likely already presenting some dementia. While potentially helpful in confirming general dementia, odor identification tests, especially unilaterally and without the distinction of the aromas being pure are worthless in diagnosing AD. Odor identification per se, simply has not proven to be helpful in detecting AD.

Thus, at least two pure odorants, or a plurality thereof, may be cascaded without requiring the subject to identify any of the aromas and the screen will still generate valid results. Should a subject spontaneously name a pure odorant, no harm is done, but it is not required that the aroma be named or is it helpful to obtain valid results.

Cascading Aromas, an Preferred Alternative Aroma Detection Screening Metric;

Cascading a sequence of a plurality of pure aromas without a pure air reset period between aromas also scales the relative olfactory thresholds of the nostrils and has distinct advantages. The aromas may be presented manually where the aroma device is advanced to present a fresh aroma as the previous aroma is consumed or the device may be mechanically spring loaded, where the aromas are changed at the push of a button by the test subject during the screen. Alternatively, more than one device may be used to present the more than two odorants, or pure odorants to the patient.

The olfactory function of dissonance is far faster than "resetting" with a time delay, such as is required to reach a "no aroma detection condition" using clear air in preparation for a next aroma test event. The human olfactory latency period between having sensed a first aroma and being able to switch to sense a second aroma is far faster than going from aroma laden air to clear air.

The ability to ignore a first aroma and fully concentrate on a second aroma is of significant utility in using a cascading pure aroma threshold testing method. This method uses a metric of "rapid sequential aroma scoring". "Cascading" a plurality of pure aromas, presented one immediately after another, ignores the currently required 90 second reset period between aroma presentations. This method speeds up the overall bilateral aroma testing process dramatically, as well as reducing scent latency issues.

The period of time, we shall call the "olfactory threshold latency period" is an indirect measurement of the condition of the olfactory nerve, which is of clinical significance in detecting localized deterioration of the brain. Adding a number of such latency periods together creates a larger sample from which to more finely deduce the relative sensitivity of the nostril. Enlarging the aroma presentation device from 1 liter to 1.5 liters will increase the number of breaths or the number of seconds it takes to note a fresh aroma. While the mean number of breaths with a 1 liter aroma device appears to be 4, 50% more volume will increase to 6 the average number of breaths per event.

Aroma presentation devices without an aroma chamber, such as the one presented in FIG. 10 and higher, reduce the time spent breathing aroma infused air and allow an interesting plurality of aromas to fade in and out quickly.

The longer the latency period of one nostril, the weaker the sense of smell in that nostril. What we seek to detect is a significant relative deficit, particularly on the left side rather than an absolute value.

Theoretically, and according to previous clinical testing, the longer the period of time between exposure to aroma infused air and cognitive notice of that aroma, the worse the olfactory deterioration is in a particular nostril. The more time that is required to note the aroma, or a higher concentration of aroma required to trigger cognitive notice of that aroma, when tested bilaterally indicates relative olfactory deterioration of the two sides. More breaths equal more time and relative olfactory deterioration of the nerves associated with one nostril.

The memory function of an aroma, once cognitively recognized, (not necessarily named) remains in the olfactory "Que.", until replaced by a subsequent aroma. It is thus, very hard to concentrate on smelling more than one aroma at a time. The new aroma replaces the previous aroma in our active olfactory memory.

"Olfactory aroma memory latency", presents potential issues using a single aroma vs the clear air (air with no detectable aroma) mode of testing. It is hard to forget the recently presented aroma when only compared with theoretically clear unscented room air, making us hypersensitive to any latency of the first aroma. Unscented air in that method of testing must be used to purge the olfactory nerve and the aroma presentation device of latent aroma in preparation for the next testing event. Olfactory aroma latency is defeated by cascading a plurality of at least two pure odorants without a reset period.

A "reset" of the olfactory nerve may be defeated by even the slightest hint of the recently presented aroma. Aroma which is still lingering in the air or clinging to the airways of the aroma presentation device or the nostril can easily contaminate otherwise clear room air and spoil the sensitivity of the test. This is really the downfall of a one aroma screen.

While the recently presented aroma may be very faint after a reset period, the human sense of smell in some people is amazingly strong. The aroma latency issue thus creates a potential problem in obtaining accurate bilateral olfactory threshold sensitivity data with a clear air baseline sort of test.

Faint mechanical latency and human aroma memory latency issues, when using a handheld aroma presentation device, may be successfully overcome by "cascading" a new pure aroma immediately after another without using a clear air "palate cleansing" interval between aroma testing events. As soon as a first aroma is detected a subsequent aroma is strongly presented causing the first aroma to fade from memory without the problematic and time consuming step of clearing the olfactory "palate" with clear air.

A metric for bilateral olfactory threshold cascading testing is provided:

The testing method and scoring metric of finding the sum of at least two olfactory threshold detection periods, corresponding to at least two pure odorants, in seconds or in the number of breaths, derived from presenting a series of pure aromas, presented sequentially one after another. The aromas are presented in rapid order to one nostril, without clearing the olfactory nerve with unscented air between pure the aromas. While using as few as 2 aromas may provide meaningful clinical data, since there are so many pure aromas to choose from a plurality of even 20 such aromas develops a more interesting test and extends the test cycle which also presents more defined nostril sensitivity differentials.

The identical test is then run on the other nostril and cumulative results compared to scale the bilateral pure air aroma detection thresholds of the patient. When the test subject notes that a new aroma is sensed, the device is immediately advanced to the next aroma either manually or automatically with a spring loaded, indexed sort of mechanical arrangement. A circular presentation method where the first aroma is also the first and last sample presented has clinical merit.

A method for cascading aromas for aroma presentation devices with an aroma chamber.

A first aroma is presented and the test subject told to take three breaths, upon the third exhalation, the device is advanced and the second aroma is immediately presented.

When the second aroma is sensed, a third aroma (if used) is immediately presented etc. This is done without a "reset period" using unscented air between the pure aromas presented.

A Method for Cascading Aromas

A first aroma is presented and the test subject told to take three breaths, upon the fifth exhalation, the device is advanced and the second aroma is immediately presented.

When the second aroma is sensed, a third aroma (if used) is immediately presented etc. . . . . . This is done without a "reset period" using unscented air between the pure aromas presented.

A few as two pure odorants may be used by cycling between them. Alternately, a large plurality of different pure aromas may be used. When the plurality of aromas have all been presented and the device has cycled back to the first aroma, the cumulative time elapsed clock is stopped and the seconds for that nostril recorded or the number of breaths taken is noted. Thus, the time in seconds between start and stop tones becomes the metric to be recorded for that nostril. Alternately, the sum of number of breaths per aroma is added up to scale the nostril being tested.

An audible tone may also be emitted during the exhalation portion of the breath cycle so testing personal can be aware of the number of breaths taken during the testing process and be aware of potential hyperventilation and the number of breaths taken between tones is also a metric that may be of some utility.

The patient may be asked to count breaths if the cascading device is manually advanced. The subject may take an additional breath to confirm that the aroma has changed but will be asked to state the number of breaths taken before they actually noted the fresh aroma. The number of breaths is recorded for each nostril.

A battery of olfactory threshold testing for both nostrils may thus be performed very quickly if a plurality of pure aromas are presented one after another, immediately after each fresh aroma is detected, rather than waiting for the subject to recognize that there is "clear air" or the complete absence of aroma residual or latency.

Utilizing a cascading aroma method means that the newly presented aroma concentration seems much stronger than any faint latent aroma from previous aromas, thus overcoming both human and mechanical latency issues with the additional advantage of speeding up the testing process dramatically by abandoning a reset period between aroma events.

The plurality of pure aromas used may be placed in any order that puts the most distinct odors between similar but different aromas to help the subject differentiate between the aromas. Actual clinical testing has been done cascading from 3 to 6 pure aromas with statistically similar results.

Any number of aromas may be used as long as the aroma is advanced upon cognitive notice of the instant aroma. As few as two aromas may be used alternatively, but 6 or even 8 completely different aromas in sequence may be used with this method of testing. Completely changing the aromas is more far interesting to the subject than alternating between only two or three aromas.

If, as in the previous example, using 1.5 liter aroma chamber, the subject averaged 10 seconds per aroma presentation, before cognitive recognition of a fresh aroma had taken place, a complete test battery of 10 events per nostril could be done on both nostrils in about 3 minutes.

Alternatively, rather than measuring a plurality of pure aroma detection periods in seconds, the number of breaths it takes to advance from the first aroma sequentially back to the first aroma is an alternative metric. In other words, 25 breaths for the left and 18 breaths for the right is a meaningful scoring method. The breath tones sounds emitted are to allow supervision of the test procedure by clinical staff members.

The cognitive load factor is much less when the subject simply notes that a new aroma is detected by pushing a momentary button to advance to the next aroma, rather than remembering exactly what the aroma is and cognitively coming up with the name for it. Simply mashing a button upon noting a fresh aroma has been smelled is very intuitive and easy to learn.

Lacking an automatic aroma cascading mechanism, the device works to offer an aroma by presenting 5 breaths, manually switch to a fresh aroma and handing the device back to the subject with the first aroma infused in a volume of air in the chamber ready to be replaced by further inhalations. The number of breaths it takes to consume the first aroma contained in the aroma testing device until a fresh aroma is pumped up to the nostril indirectly increases the concentration of the fresh aroma as the first aroma cases away until cognitive notice is achieved. The process is repeated for further aroma presentation events and the results noted.

The Cascading Aromas Device

The described hand held aroma detection device present a much more likely commercially viable embodiment of bilateral aroma testing for widespread clinical use than the larger afore mentioned desktop units or peanut butter and ruler as an apparatus. The handheld device, potentially removably clipped to a plaque on the wall of an examining room presents the notion of aroma testing being suitable for widespread, general clinical use as a neurological screening tool.

However, the aroma presentation device and aroma media might be disposable, which has the advantage of using a sterile device for each patient, having a fresh device would eliminate latent aromas and the cost of a disposable screening device might be commercially more profitable than reusing it for multiple patients.

A multiple aroma cascade presentation device might be designed such that the test is self-administered. The person being tested would simply hold the device comfortably up to their nostrils, close their eyes and press a button on the handheld device to automatically advance to the next aroma immediately upon noting the current aroma being presented to them. One first nasal cannula would present an aroma while the other second cannula would provide clear air. The device might be symmetrical such that it only need be taken away from the nostrils and reversed to make the second nostril the one presented aroma while the first nostril receives fresh air.

A series of tones could signal the starting point and ending point of the plurality of aroma presentations. A distinct audible tone, such as a dinging sound, is sounded when the first aroma is presented and when the last aroma is noted. The tones are to allow time interval measurement by the clinical staff members as opposed to counting breaths.

A distinct "exhalation tone or honking noise" could indicate that a breath has been exhaled. The handheld aroma presentation device emits an audible tone during exhalation to make the testing personnel aware of the breathing pattern of the subject.

A multiple chambered pure aroma or pure odorant cartridge may be mechanically spring loaded to advance in only one direction, one aroma chamber at a time. The multi cavity aroma media is rotated into alignment with a single airway communicating with the nostril, the device automatically advancing to the next aroma sample when actuated by pushing a control button.

With a hand held aroma presentation device without an aroma chamber, a first aroma is presented and the subject is told to breath normally and then push a button conveniently located on the hand held aroma presentation device when they smell the aroma. A tone may be emitted by the device as it advances to the second aroma and a visual readout would confirm the aroma chamber in alignment with the airway for the test administrator to observe.

A multiple chambered pure aroma or pure odorant cartridge may be mechanically spring loaded to advance in only one direction, one aroma chamber at a time. The multi cavity aroma chamber is rotated into alignment with a single airway communicating with the nostril, the device automatically advancing to the next aroma chamber when actuated by pushing a control button.

A first aroma is presented and the subject is told to take 5 breaths and then push a button conveniently located on the hand held aroma presentation device. A tone may be emitted by the device as it advances to the second aroma and a visual readout would confirm the aroma chamber in alignment with the airway for the test administrator to observe.

Upon advancing sequentially though all the aromas, back to first aroma, pushing the button to indicate that the first aroma (and last) was noted, a discrete audible tone indicates that the first (and last) aroma has been noted. The time sequence is stopped at that instant, the period in seconds between tones is the metric recorded for that nostril.

The timer may be a computer device, stop watch or a timer disposed and integrated into the hand held aroma presentation device.

Alternatively, the aroma presentation device might be manually adjusted to present one aroma at a time for the counting of breaths to the point of noticing a fresh aroma. The same device might also contain a plurality of aroma chambers such that an aroma identification test with more than 20 aromas supported might be done with the device.

The number of seconds can be counted from the first breath taken through the plurality of aromas until the first aroma is recycled to the last aroma, which is the stopping point of the test. For laboratory testing purposes a simple gas flow meter might be placed in line with the air inlet port to confirm that a uniform flow of air is being inhaled for each nostril being tested.

The number of seconds can be counted from the first breath to the breath where the fresh aroma is noted. For laboratory testing purposes a gas flow meter might be placed in line with the air inlet port to confirm that a uniform flow of air is being inhaled for each nostril being tested.

Dealing with Aroma Latency Issues

Such hand held aroma presentation devices that sequential offer pure air as opposed to aroma laden air and then reset back to pure air can have the previously mentioned "mechanical aroma latency" issue.

When a slight hint of the single aroma being used is still detectable by the test subject in the optimally pure air, it is a "mechanical aroma latency issue" as opposed to human latency factors.

Aroma latency in either form, mechanical or human aroma memory, nullify or distort the testing perimeter. Mechanical aroma latency creates issues in accurate testing of subjects who can even slightly smell the previous aroma for any reason in the clear air provided, before the device ought to deliver the aroma-infused air for a controlled testing event.

Materials with a molecularly rough textured surface or a "high surface energy" airway might tend to capture aroma molecules which may later be detectable in the otherwise clear air. Thus, smooth surfaces and low energy surface are preferred to allow most aroma molecules to pass by without adhering to the airways of the device.

The mechanical aroma latency effect is exacerbated by potential human odor memory, which makes one particularly sensitive to a single previously smelled odor for a period of time that may be much greater than a 90 second reset period.

Overcoming both human and mechanical aroma latency issues in handheld aroma presentation devices are addressable in the following ways.

1. Reduce the aroma concentration and volume used as aroma sources to the bare minimum amount of pure aroma required to accomplish the test function.

2. Using an ideal aroma formulation for the purpose of the test may mitigate mechanical aroma issue significantly.

3. Using a cascaded aroma testing method does not require a pure unscented air mode significantly nullifies the effect of trace amounts of latent, previously presented aroma as a second, stronger aroma masks the far weaker previously presented, but still faintly latent previous aroma 4. Using a plurality of aromas without switching to a pure air presentation will tend to also overcome human aroma latency by replacing the latest aroma held in odor memory with a fresh aroma 5. Mechanical design minimizing surface areas exposed to aroma infused air and special materials used in manufacturing hand held aroma detection devices would also tend to further mitigate mechanical aroma latency issues using materials that do not attract aroma.

6. Clear air pathways could pass through filtration or electrostatic plates to remove airborne aroma molecules 7. Using a disposable device allows a perfectly clean device for each screening 8. It may be possible to wash the device to remove old aroma adhered to the parts.

Oleophobic airway parts and potentially even the device hollow body that is exposed to aroma laden air could reduce significantly mechanical aroma latency since "nothing sticks to teflon". The aroma latency effect nullification by oleophobic materials is due to aroma molecules being repelled by such surfaces rather than being attracted by them, as is the case with many common plastics, such as PVC. Having a low surface energy airway gives passing aroma no place to "stick" on a molecular level so it passes by without contaminating the surface of the airway. Manufacturing aroma devices where air pathways and potential the entire interior of the device's hollow body are produced using a class of oleophobic materials provide less aroma contamination potential. This class of material will significantly reduce or practically eliminate mechanical aroma latency due to surface attraction of aroma molecules.

Lining air pathways with oleophobic interior coatings or using Teflon surfaces in places exposed to aroma could thus dramatically reduce mechanical aroma latency issues.

The non-exhaustive group of such preferred plastics and specialty materials that would tend to reduce the effect of capturing stray aroma molecules include; Teflon class plastics, silicone materials and a number of oleophobic coatings and resins. Oleophobic coating and resins may be applied to metal, glass or ceramic hollow body surfaces used as hand-held aroma testing device hollow body parts or airways.

Some oleophobic resins require "firing" at up to 700 degrees F., which would preclude manufacturing aroma presentation devices with plastics and using such resins. Further, the oleophobic effect of Teflon class plastics is fundamentally as strong as even the very best such resins and coatings.

Teflon class plastics such as PFA (Perflouoroalkoxy), PTFE (Polytetrafluoroethelyne) and FEP (TetraFluorEthylene-Perfluorpropylene) may be obtained in clear, white or colors and may be extruded, injection molded, die stamped or blow molded, thus enabling preferred methods of device mass production and support attractive industrial designs. Other plastics having a relatively low surface energy, and thus likely to repeal aroma in contact with the material are, polystyrene, polyethylene, Tedlar, PVA, EVA and Acetal coatings of oleophobic resins.

Alternatively, rather than repelling aroma molecules using oleophobic coatings or materials as mentioned above, electrostatic resins or electrically charged plates could capture stray aroma molecules to prevent the clear air from being contaminated by latent aroma from previous aroma presentations.

The preferred materials and design embodiment for controlling latent aroma must clearly be repelling latent aroma molecules in the first place, rather than trapping them. Filtration media such as baking soda filters or absorbent airway coatings, activated charcoal filtration, electrostatic filtering mechanisms and electrostatic resins all ultimately reach a maximum aroma holding capacity and must be cleaned or filters replaced to keep the aroma presentation device working as designed. This is not a preferred embodiment.

Oleophobic solutions would tend to minimize contamination of the device by aroma latency in the first place. Such devices would be much easier to clean, potential refreshed with a simple occasional wipe down with a disposable paper towel. Better to avoid the aroma contamination in the first place than to concentrate it in filters to control the pure air contamination.

When a plurality of aromas are used, mechanical aroma latency countermeasures as described above would largely prevent a detectable latent aroma situation, since the newly presented aroma would be much stronger than the previously offered aroma, a latent amount that might be only slightly detectable in clear air but not at all compared to a fresh strong aroma.

Minimizing surface areas present less material to be contaminated. So design can also mitigate aroma latency issues.

Multi-Aroma Chambered Devices

A hand held aroma presentation device might have a plurality of aroma chambers, which can be mechanically rotated or selectively re-aligned in a way as to present an open pathway for only one aroma at a time. Such a hand held screening tool is a very desirable apparatus.

Aromas are presented sequentially while closing access to all other aroma chambers. Such a device would speed up the testing procedure dramatically and reduce or eliminate significant aroma latency issues.

The person being tested would inhale through the aroma testing device to bring a plume of aroma infused air through only one of the plurality of aroma chambers. The aroma passing through the device air pathways into a nostril specula are presented directly into the test subject's nostril.

The improved hand held aroma presentation device described herein, might have 20 or more separate aroma chambers. Each chamber will selectively rotate in line with one airway port which is in fluid communication with the nostril of the person being tested. Each aroma chamber has a felt like pellet or disk held in place that holds a drop or more of aroma fluid. The active airway draws air through the absorbent pellet or disk to infuse pure ambient air with an aroma.

The clinical employee or even the person being tested simply rotates an aroma presentation selector to align the single airway with the next aroma in sequence. The device is advanced immediately upon the test subject noting a fresh aroma was detected. When the number of screening events required are completed the cumulative elapsed time or number of breaths taken is recorded for each nostril and compared for a clinically significant difference.

The same device may be used in scent identification where the aromas are numbered such that the testing personnel can supervise the test as the subject checks off one of 4 or 5 possible aromas they smell through the device. The device may then be reversed to check the other nostril as 20 or more aroma are presented.

The aroma presentation device holds the multiple cavity aroma chamber part in rotational alignment or in liner alignment with the hollow body. The segmented aroma chamber part or disk in one embodiment can potentially only rotate or move in one direction to advance the aromas and clicks in place to mechanically allow the single airway path into the hollow body to be aligned with only one of the aroma chambers at a time.

Ergonomically located on the exterior of the aroma testing device may be a button. The control button is mechanically disposed to swiftly advance the aroma chamber to the next aroma upon the button being depressed. A tone may be emitted to denote advancement to the next aroma. A special tone is emitted upon advancing from the first aroma to the second aroma etc. A digital or mechanical timer may be included which times the period from the second aroma being presented until that point cycles again.

The aroma chamber device may be spring loaded with a coil type spring, a small motor or other mechanical device which upon the button being pushed advances the aroma chamber to the next station. Ratcheting gears known to the art may be employed to insure that the aroma chamber only advances in one direction. The audible tones may be electronic or mechanical with one tone to denote each new aroma as it is presented and a second distinctive tone is emitted at the presentation of aroma #1 when it appears as the final aroma.

The exhalation airway is arranged such that an audible tone is emitted whenever the test subject exhales. The number of exhalations required to complete the test may be a metric of some interest. The number of breaths for each nostril may also be helpful in insuring that the person was breathing equally through each nostril and not hyperventilating.

Each multi-cavity aroma cartridge comprises separate chambers for holding at least two odorants or pure odorants, one odorant or pure odorant per chamber, but may hold 20 or more odorants, pure odorants.

Using the proposed rapid presentation or cascade of a plurality of pure aromas as a testing perimeter and metric also solves the problem of clearing the aroma testing device chamber and pure air pathway of a single aroma to return it to a clear air mode in preparation for the next aroma presentation testing event. This issue is seen most profoundly in the clear air vs single aroma mode of testing.

The sequential aroma cascade method simply does away with the clear air mode entirely in favor of effectively resetting the olfactory nerve by presenting a fresh aroma through the faster olfactory "reset" phenomenon of sensory dissonance.

Using the plurality of sequentially presented aromas as a testing method actually simplifies the mechanical device required to present the aromas and manage the testing events. Not being required to revert to a clear air mode between testing events nullifies the need for a number of parts in many embodiments of previous handheld aroma testing devices using only one aroma. Devices with a plurality of aromas also does away with the requirement of a large aroma chamber in favor of simply passing clear air through a plurality of aroma containing felt like elements.

A removable multi-chambered aroma element could be sold as a consumable test element allowing for an easy way to refresh the device. After one or more aroma tests have exhausted the rotating aroma multiple cavity cartridge or disk, is disposable. The replaceable cartridge or disk contains a plurality of fresh pure aromas especially formulated at the factory to work well with the aroma presentation device. Seals covering ports in the multi cavity aroma chamber are removed and the fresh aroma cartridge is installed. Alternatively, the entire device is disposable. The aroma media disk disclosed may use actual essential oils and preserve them for a considerable shelf life due to release strips sealing the aroma in a small chamber holding an absorbent felt like member that allows air flow through it to infuse air with the aroma.

Figures 2, 3:
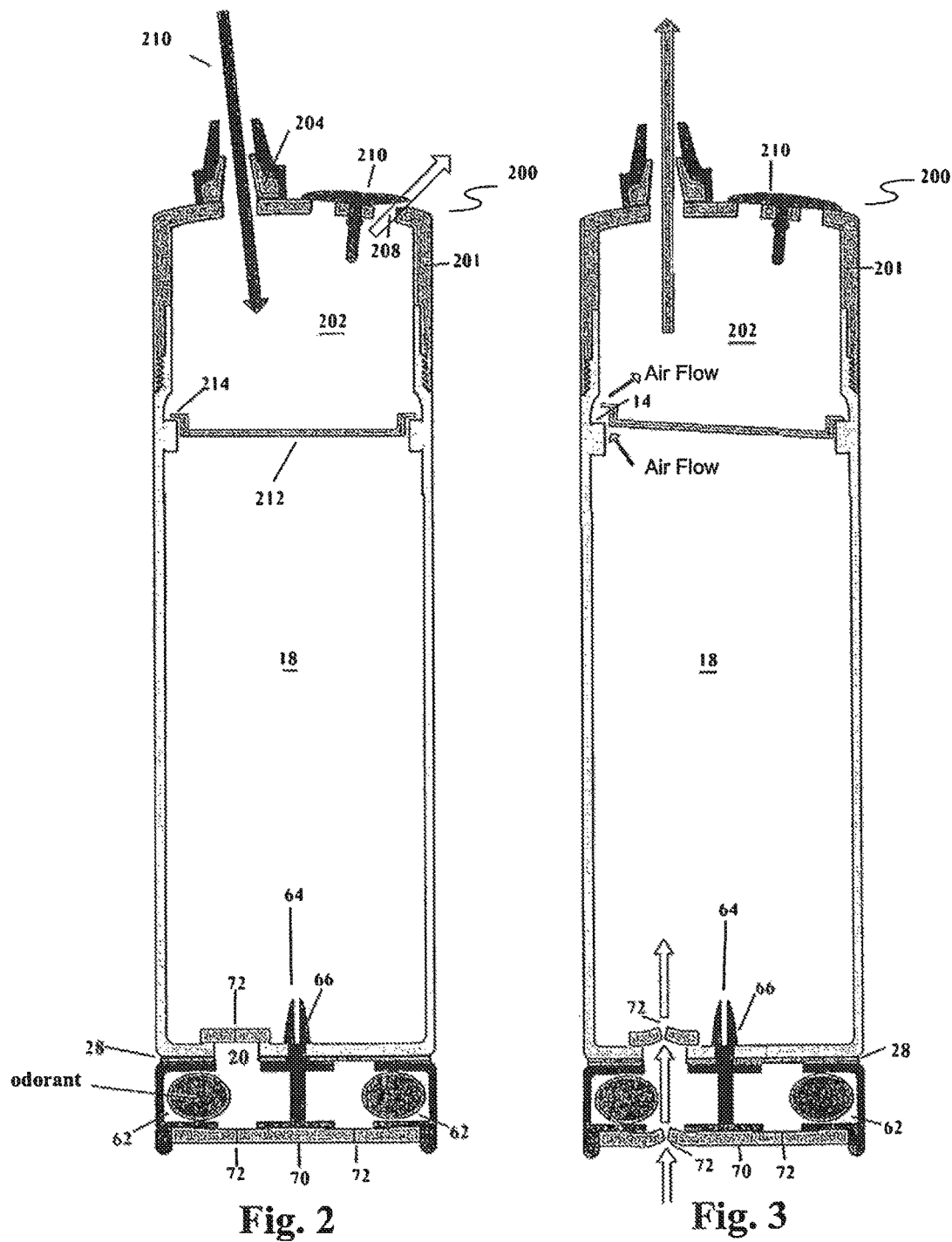
FIG. 2 illustrates a cross-sectional front view of the embodiment of FIG. 1 in exhalation mode.
FIG. 3 illustrates a cross-sectional front view of the embodiments of FIGS. 1 and 2 in inhalation mode.

FIGS. 1-3 provide a housing 10 and a cap 200. Housing 10 comprises a top lip 12 defining an inner shoulder 14 and outer threads 16. Housing further defines inner air chamber 18 having an air inlet 20 disposed therethrough that may be located on bottom surface 22 of housing 10. Bottom surface 22 of housing 10 may further comprise an connection aperture 24.

The embodiments of FIGS. 1-3 further comprise an upper gasket 28, affixed to the outer lower surface 26 of the housing 20 and comprising a shape generally the same as the shape of the housing's lower surface 26 and further comprising air inlet aperture 30 and connection aperture 32 therethrough. Air inlet aperture 30 matches and is aligned with the air inlet 20, allowing fluid communication therethrough while connection aperture 32 matches and is aligned with connection aperture 24.

The embodiment shown in FIG. 1 further comprises an advancer mechanism 40 that comprises an upper surface and a lower surface, wherein the upper surface is attached to the upper gasket 28 and may comprise advancer button 42. As shown in FIGS. 6A and 6B, advancer mechanism 40 may comprise a ratcheted gear mechanism 44 as is well known in the art, or alternatively, a wound spring mechanism 46, or clock spring mechanism, as is also well known to the skilled artisan. These exemplary mechanisms ensure that, when advanced by actuating the advancer button 42, the pure odorant or pure aroma cartridge advances in only one direction. Advancer mechanism 40 comprises an air inlet aperture 47 and a connector aperture 48, wherein air inlet aperture 47 is matched and aligned with air inlet aperture 30 of upper gasket and connector aperture 48 is matched and aligned with connection aperture 32 of upper gasket.

The embodiment of FIG. 1 further comprises a lower gasket 50, affixed to the lower surface of advancer mechanism 40 and comprising the same or similar features as the upper gasket 28, i.e., an air inlet aperture 52 and connection aperture 54, wherein air inlet aperture 52 matches with air inlet aperture 47 of advancer mechanism 40 and connection aperture 54 matches and is aligned with connection aperture 48 of advancer mechanism 40.

The embodiments of FIGS. 1-3 comprise a pure odorant cartridge 60 that is rotatably affixed to the lower surface of lower gasket 50 and comprises at least two odorant chambers 62. The embodiment of FIG. 1 further comprises the odorant chambers 62 being capable of rotating into individual fluid communication with air inlet aperture 52 of lower gasket 50.

Figure 5A:
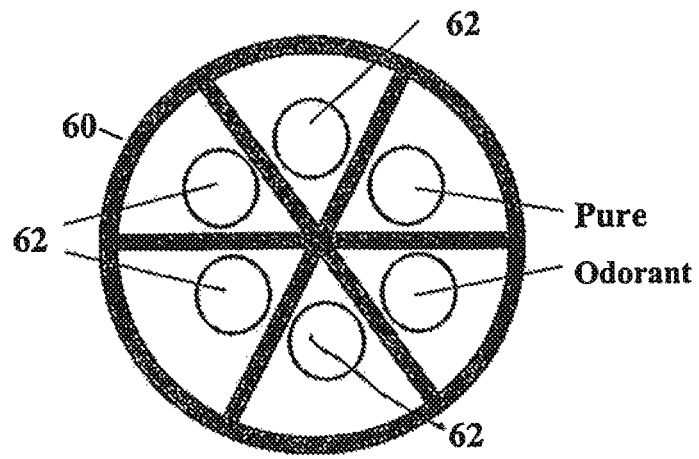
FIGS. 5A and 5B illustrate a top view of two embodiments of a multi-chamber odorant or pure odorant cartridge.
Figure 5B:
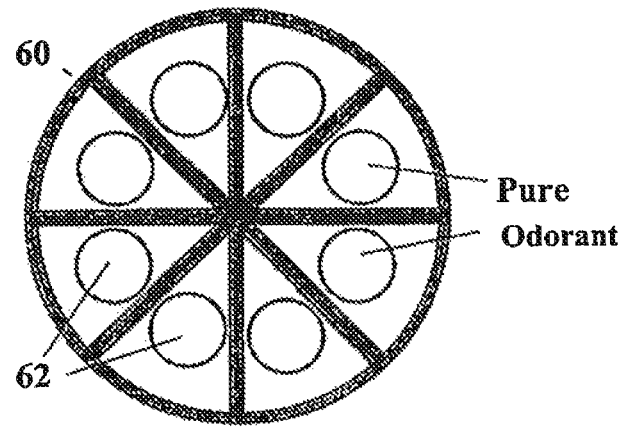

For each illustrated embodiment of FIGS. 1-3, and as shown in FIGS. 5A and 5B, six or eight, or any other number larger than one, odorant chambers 62 are provided. Pure odorant cartridge 60 may comprise a central axis 64 around which the rotatable pure odorant cartridge 60 rotates.

Central axis 64 comprises a top connector 66 which is rotatably aligned within connector apertures 52, 48, 32 and 24 in the embodiment of FIG. 1.

Top connector 66 thus engages connector apertures 52, 48, 32 and 24 providing a snug fit of all components described above against lower surface of housing. Application of sufficient downward force will overcome the engagement of the top connector 66, thereby allowing the pure odorant cartridge 60 to be removed. Consequently, it is possible to reload a spent pure odorant cartridge 60 and replace it with re-engagement of top connector 66 with connector apertures 52, 48, 32 and 24. Alternatively, a pure odorant cartridge 60 that was previously loaded with pure odorant in odorant chambers 62 may be engaged with connector apertures 52, 48, 32 and 24. The embodiments in FIGS. 2 and 3 do not require advancer mechanism 40 or lower gasket 50.

Figure 7A:
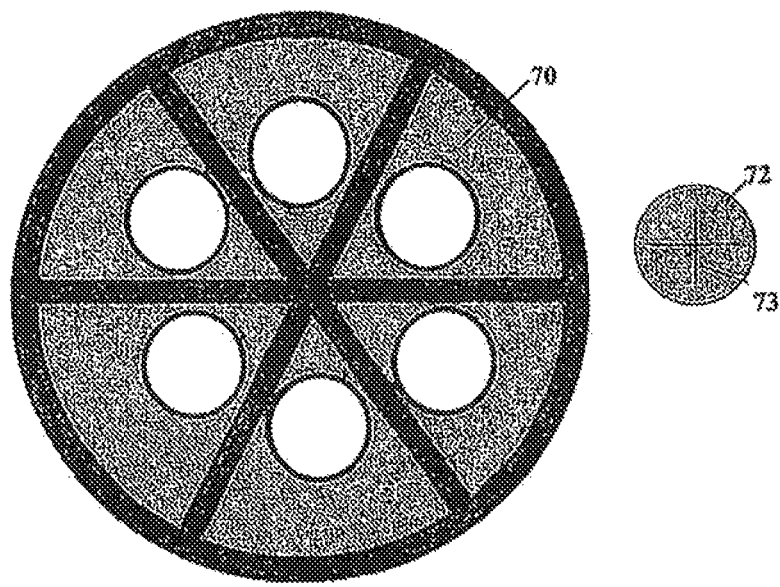
FIG. 7A illustrates one embodiment of a valve member sheet.
Figure 7B:
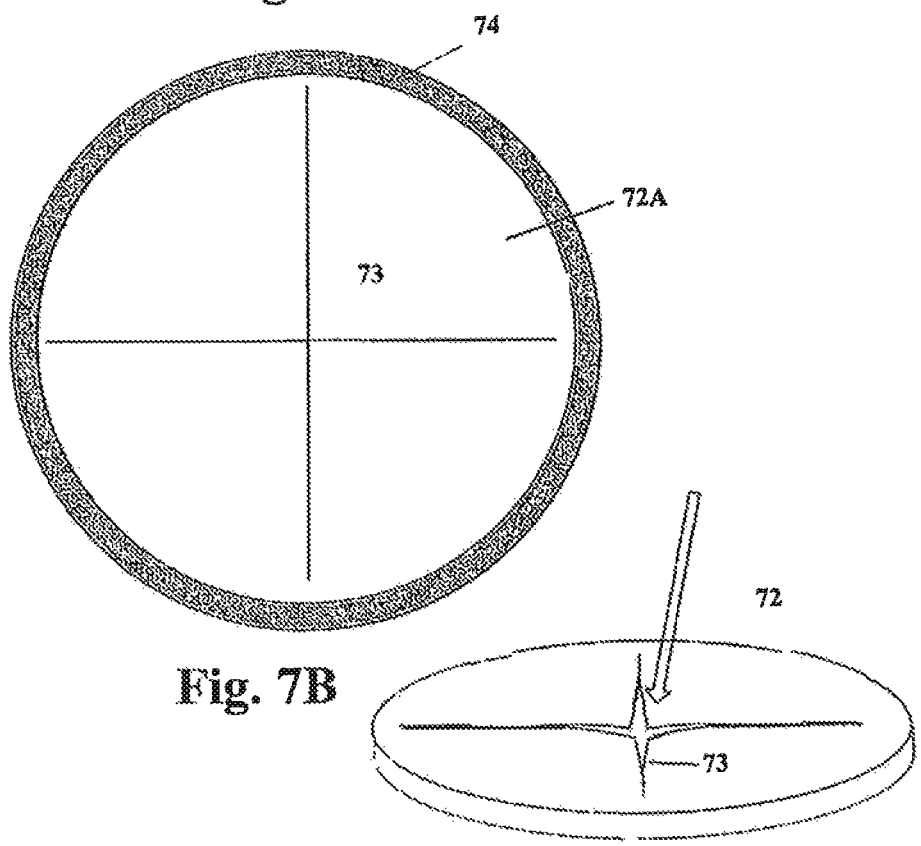
FIG. 7B illustrates one embodiment of an individual valve member.

Lower surface LS and in some embodiments, upper surface 68, of pure odorant cartridge 60 may be covered with an adhesive layer 70 comprising valves 72 aligned with the pure odorant chambers 62 as in FIG. 7A. Valves 72 may comprise resilient flaps 73 cut through the valve material, e.g., silicone or rubber, to allow air flow therethrough. This layer prevents escape of the pure odorant within the chambers 62, but allows air flow therethrough. Alternatively, individual valve elements 72A, generally of the same construct as layer valves 72, may be provided as illustrated in FIG. 7B. Such valve elements may comprise an outer adhesive portion 74 to cover the related chamber 62.

Pure odorant cartridge 60 may rotate by aid of the advancer mechanism 40 described above or, alternatively, advancer mechanism 40 may be bypassed or be eliminated altogether. See, e.g., FIGS. 2 and 3 for manually rotatably advanceable embodiments. In either case, pure odorant cartridge 60 may be rotatably advanced manually, aligning an initial pure aroma chamber 62 with air inlet aperture 52 of lower gasket 50.

With reference to FIGS. 1-3, cap 200 comprises a body 201 defining a chamber 202 therein, a nasal port 204 and nasal port lumen 206 within nasal port 204, wherein nasal port 204 is in fluid communication with chamber 202 and with the atmosphere outside the nasal port 204. Nasal port 204 may be covered by a removable nasal specula 205 or the equivalent.

Cap 200 further comprises threads 207 that are capable of threaded communication with outer threads 16 of housing. Other methods and mechanisms for joining the cap 200 with the housing 10 are certainly within the scope of the present invention. Moreover, an alternate one-piece construction with cap merged with housing is also within the scope of the present invention. Cap 200 further defines at least one exhalation valve opening 208 through the cap body 201 which is shown with a resilient valve 210 disposed over the at least one valve opening 208.

Figure 4:
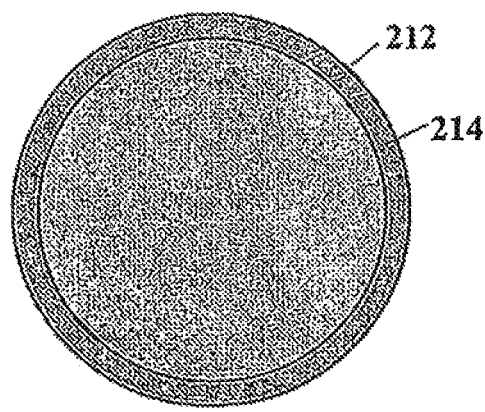
FIG. 4 illustrates a top view of one embodiment of a flap valve.

FIG. 4 illustrates a flap valve 212, having a lip 214 that rests on housing's inner shoulder 14 is provided. As known in the art, one portion of the flap valve is fixed to the inner shoulder 14, while another portion of flap valve 212 is moveably disposed on the inner shoulder 14. This arrangement allows air flow with sufficient force to lift the moveably disposed portion of the flap valve 212 upward from the housing to the cap and nasal port. It also prevents downward air flow from the nasal port and cap into the housing.

Accordingly, an exhalation air flow path is provided within cap as best illustrated in FIG. 2. There, a patient exhales through the nasal port 204 into the cap chamber 202 and out of exhalation valve opening 208, as the downward air flow is blocked and redirected by the closed flap valve 212. Alternatively, the patient may simply disengage the nostril from the nasal port 204, exhale into the atmosphere and then reengage the nostril with the nasal port 204 for a second inhalation.

FIG. 3 illustrates the active inhalation air flow path, initiated by a patient inhaling through nasal port 204 with sufficient force to enable the active path. Here, external atmospheric air flows inwardly through the valve members 72 or 72A in alternative embodiments, and into the pure odorant chamber 62 aligned therewith. The pure odorant media therein infuses the incoming air with the pure odorant aroma and the infused air flows through the aligned air inlet apertures and into the housing chamber 18. The infused air flow pressure raises the flap valve 212 to enable the infused air to flow into the cap chamber 202 and out of the nasal port 204 into the patient's nostril.

Thus, this exemplary device may be used to present a more than one pure odorant in a cascading fashion, i.e., sequentially and within a reset period between presentations. Initially, a first pure odorant is made available for presentation to one nostril of a patient, wherein the patent inhales to activate the inhalation air flow pathing described above, and exhales into the device until a fixed number of breaths are reached, or a fixed time has elapsed or until the patient recognizes they have reached the pure odorant detection threshold, whereupon the relevant metric is observed and recorded. At this point, the multi-chamber pure odorant cartridge 60 is advanced to the next pure odorant and the process is repeated and again if additional pure odorants are provided in the testing process and in the cartridge 60.

When the first nostril testing is completed, the same process is repeated with the second nostril. Ultimately, the results are compiled and the left nostril and right nostril data is compared for substantial differences between the left and right nostril data sets.

Figure 8A:
FIG. 8A illustrates a perspective and exploded view of a glass jar with threaded cap.
Figure 8B:
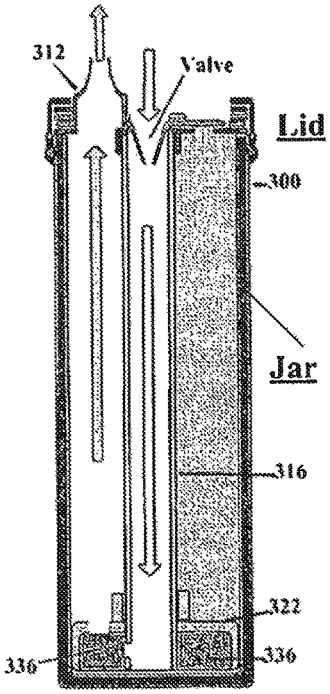
FIG. 8B illustrates a cross-sectional front view of one embodiment corresponding to FIG. 8A.
Figure 8C:
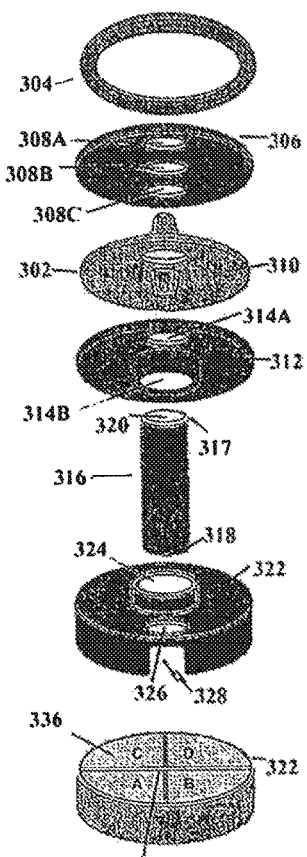
FIG. 8C illustrates an exploded view of the embodiment of FIGS. 8A and 8B.

FIGS. 8A-8C illustrate another embodiment comprising an aroma screening device 300 using an off-the-shelf glass jar with a threaded lid as a base. Lid assembly 302 comprises a die cut slip ring 304 in communication with a plastic top member 306 having a series of apertures 308A, 308B, 308C therethrough. Nasal port element 310 comprises a nasal port 312 therethrough which engages one of the apertures 308B. Nasal port element 310 is operationally engaged with plastic top member 306 and with plastic lower member 312 which comprises holes therethrough 314A, 314B. 314A is in fluid communication with the nasal port 312. A tube 316 is provided, having a proximal end 317 in fixed attachment, e.g., glued, to the plastic lower member 312, wherein the lumen 320 of tube 316 is in fluid communication with nasal port 312 and hole 314B. Distal end of tube 318 is in fixed attachment with the pure odorant chamber cover element 322 which comprises a hole 324 therethrough in fluid communication with tube lumen 320, a pure odorant chamber access aperture 326 and a pure odorant release aperture 328 disposed on a side 330 of the pure odorant cover element 322. Pure odorant cover element 322 covers pure odorant cartridge 332 which is fixed in place at the bottom of the jar. The entire assembly, aside from the fixed-in-place cartridge 332, is capable of rotation from one pure odorant media 336 within a chamber 334 within cartridge 332 to the next, or another, pure odorant media 336 within chamber 334.

Thus, a nasal port 312 is in rotatable fluid communication with a pure odorant cartridge 332 comprising at least two pure odorant chambers 334 each capable of holding a single pure odorant medium 336. A central inhalation tube 316 in valved communication with the atmosphere and with one of the pure odorant chambers 334 when the nasal port 312 is rotatably aligned with the desired pure odorant chamber 334. An exhalation path is provided as illustrated that flows downward through the valve and into the central tube 316, through the pure odorant media 336 within the aligned pure odorant chamber 334, infusing the inhaled air with the aligned pure odorant aroma. The infused air then flow upwardly through the nasal port 312 and into the patient's nostril until the patient signals reaching the pure odorant detection threshold or, in certain embodiments a maximum number of breaths and/or time is reached. Rotation of the lid assembly to another pure odorant chamber 334 allows repeat of the process without a reset period, i.e., cascading of pure odorants.

Figure 9B:
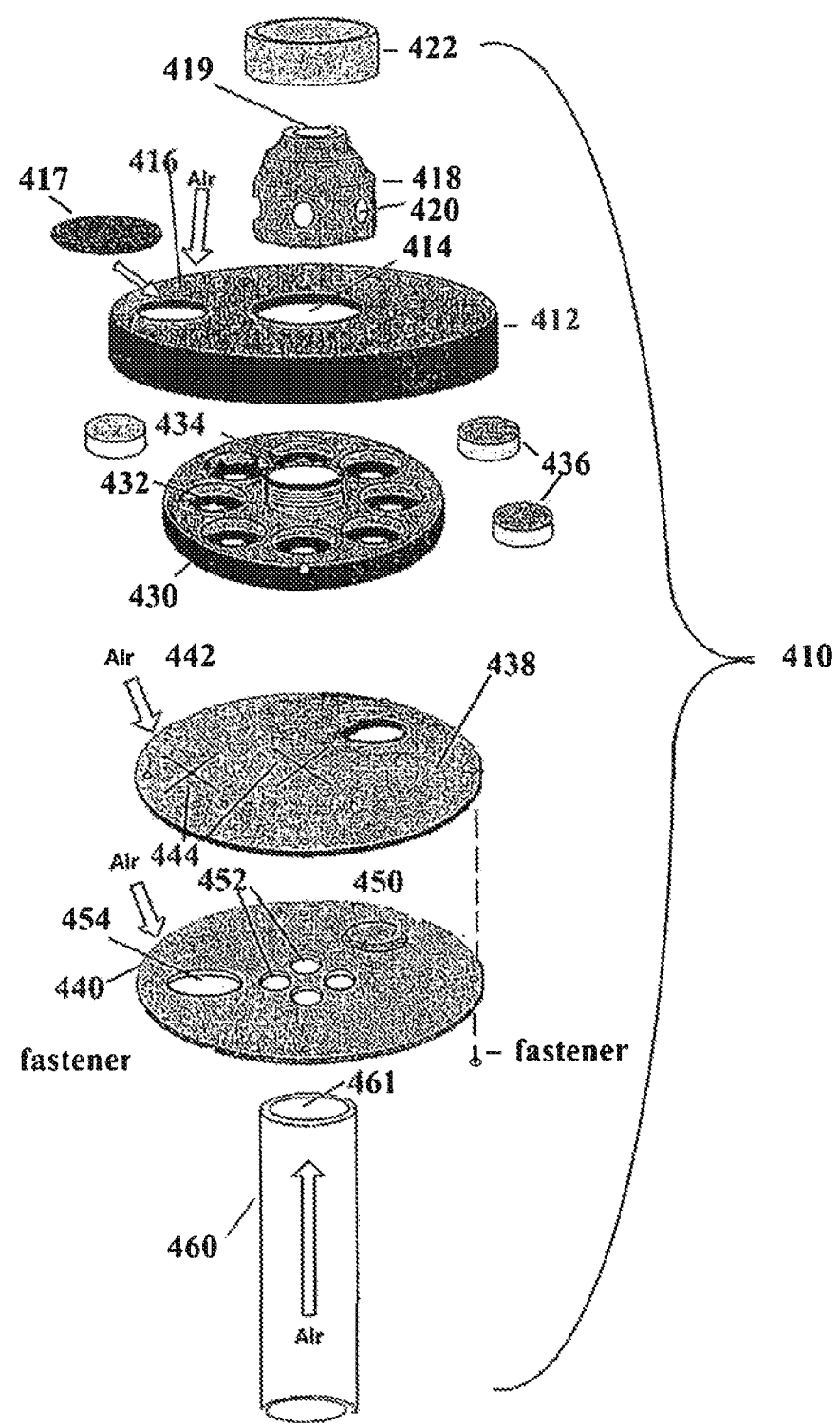
FIG. 9B illustrates a perspective exploded partial view of the embodiment of FIG. 9A.

Turning now to FIGS. 9A-9C, another embodiment of a multiple aroma presentation device 400 is provided and comprising a (preferably)) glass housing 402 defining a chamber 404 therein having an open top edge 406 and a lid assembly 410 that is fixed to the top edge 406 of the glass housing 402.

The lid assembly 410 comprises a jar lid 412 with a generally central stem opening 414 therethrough and a generally off-center air inlet port 416 therethrough covered by flap valve 417, shown removed from covering port 416 for illustrative purposes.

Lid assembly 410 further comprises a nasal tip 418 having a lumen 419 therethrough and aligned with the generally central stem opening 414 and in fluid communication thereof. Nasal tip 418 further comprises one or more exhalation ports 420, each of which are in fluid communication with the nasal tip lumen 419. The exhalation port(s) 420 are covered by a flexible circumferential valve member 422 which works as a one way valve to allow exhaled air to exit the device into the atmosphere but not allow ambient air into the device. For example, a rubber band type valve member may be used. Other equivalent valves will present themselves to the skilled artisan, each of which are within the scope of the present invention.

The pure odorant cartridge 430 comprises more than two pure odorant chambers 432 therein. The cartridge 430 is preferably circular in shape with the odorant chambers 432 arranged circumferentially. In the illustrated embodiment, eight chambers 432 are provided. A stem 434 with a lumen 436 therethrough is disposed fixedly generally centered on the cartridge 430. Stem 434 rises above the top surface T of the cartridge 430, engages the stem opening 414 of the jar lid 412 and is in fixed operational engagement with the nasal tip 418 and stem lumen 436 is in fluid communication with nasal tip lumen 419 and glass housing chamber 404. As illustrated, the nasal tip 418 might threaded for threaded engagement to the stem 434, or be otherwise fixable attached to the stem 434.

In a preferred embodiment, each chamber 432 holds a single pure odorant or aroma pellet 436 which is a cylindrical shape matching the shape of the chambers 432 in the cartridge 430. The pure odorant pellets 436 are preferably composed of absorbent material such as felt or cotton which will allow air to pass through and expose the inhaled air flow to a fluid aroma source soaked up by the absorbent material.

Lid assembly 410 further comprises a gasket 438 held between the bottom surface S of the cartridge 430 and a retaining disk 440 described further below. The gasket 438 preferably comprises a soft silicone like material which may have a shore hardness of about 40 with a thickness of about 0.125 inches, though other materials, hardnesses and/or thicknesses are within the scope of the invention. The gasket 438 allows the cartridge 430 to be rotated without opening undesired airways between the pure odorant chambers 432 and the inhalation air path which will be discussed infra. The gasket 438 have comprise holes for fasteners, e.g., screws, to pass through that hold the retaining disk and jar lid together such that the cartridge 430 is held snuggly but allowed to rotate in place. Gasket 438 comprises a flap valve 442 aligned with the air inlet port 416 and a flap valve 444 aligned with the stem lumen 436, as illustrated, each of which operate as a one way valve to enable air flow. Other one-way valve solutions will become apparent to the skilled artisan, each of which are within the scope of the present invention.

Lid assembly 410 further comprises a retaining disk 440 as described above that is attached to the gasket 438 and works to retain the cartridge 430 in such a way as to allow the cartridge 430 to rotate freely, but not translate vertically. The stem 434 engages and extends through the stem opening 414 such that rotating the stem 434 rotates the cartridge 430 and, therefore, is adapted to enable alignment of any of the plurality of pure odorant media, e.g., pellets, held in the chambers 432. The retaining disk 440 comprises an indexing bump 450 or other indexing feature on the upper surface that fits into the bottom of any one of the chambers 432 to enable alignment with a particular chamber 432. Retaining disk 440 further comprises a central orifice or orifices 452 aligned with the flap valve 444 of gasket 438 as well as a circumferential orifice 454 that is aligned with the flap valve 442 of gasket 438.

Finally, lid assembly 410 further comprises a dip tube 460 fixed centrally on the bottom surface B of the retaining disk 440 and comprising a lumen 461 therethrough. The dip tube 460 may be glued in place and is in fluid communication with the stem lumen 436 and nasal tip lumen 419 as well as the glass housing chamber 404. Further, or in the alternative, a nipple 462 may be fixed on the center bottom B of the retaining disk 440 that holds, or assists in holding, the dip tube 460 in place. The dip tube 460 may be an extruded plastic tube that repels aroma, such as Teflon.

The interior surfaces of the device may be coated with an aroma repellant material to help control mechanical latency due to a build-up of aroma molecules on internal airways. One such molecularly repellant material has been invented at Harvard University. It is anticipated that super repellant materials might exceed the ability of oleophobic materials such as Teflon by up to 20 times the capacity of low energy plastics.

Thus, a cascading of pure odorants may be achieved, without a reset period between presentations of the different odorants. As shown in FIGS. 9A and 9B, the cartridge is preloaded with at least two pure odorants 436. The illustrated cartridge 430 comprises eight chambers 432 for pure odorants. The desired first pure odorant chamber 432, with desired first pure odorant 436 therein, is aligned with the inlet port 416 of the jar lid by rotating the lid assembly 410. The subject then engages the nasal tip with a nostril and inhales, thereby initiating an inhalation air flow wherein atmospheric air enters the jar housing at the air inlet port, passing through the air inlet valve, through the first pure odorant chamber 432, where the inhaled air becomes infused with pure odorant. The infused air then passes through the flap valve of the gasket 438 and the orifice of the retaining disk 440 and then enters the dip tube 460. The infused air flows upwardly through the dip tube 460 and through the nasal tip lumen into the subject's nostril where the infused air is inhaled and cognitive processing begins. The subject may exhale directly into the nasal tip where, as shown in FIG. 9C, the circumferential valve allows the exhaled air to release into the atmosphere. The subject then inhales air infused with the first pure odorant again. The process is repeated until the patient signifies achieving the pure odorant detection threshold. The cartridge is rotated to the next pure odorant in the test and the inhalation/exhalation process is repeated until reaching the pure odorant detection threshold. The metric measuring the reaching of the detection threshold may be measured in number of breaths and/or in time.

Turning now to FIGS. 10A-13B, a pure odorant presentation device 500 is provided that supports an exchangeable pure odorant cartridge 501 containing at least two pure odorants for various scent testing purposes. The device 500 consists of an openable body 502, e.g., hinged and capable of holding the pure odorant cartridge 501, a dual nostril port 504 comprising an active nasal path and a passive nasal path, capable of engaging left and right nostrils of a subject at the same time, an optional internal cartridge rotational system which may be button actuated. Alternatively the cartridge 501 may be manually advanced. An advancement button 508 capable of actuating advancement, a readout means to display aroma information to testing personnel and an aroma media disk rotation control button. The active nasal path enables fluid communication between a first nostril, engaged with the nostril port 504, and a selected and designated pure odorant while the passive nasal path enables fluid communication between the second nostril and the atmosphere.

Figure 10A:
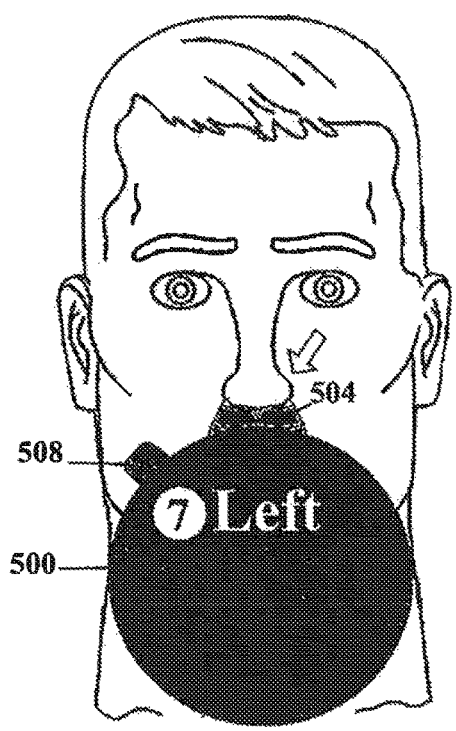
FIG. 10A illustrates a front view of one embodiment of the present invention with active left nostril odorant or pure odorant pathing.
Figure 10B:
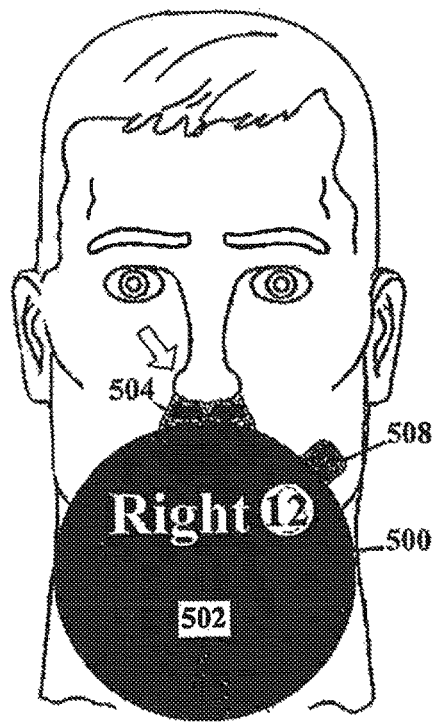
FIG. 10B illustrates a front view of one embodiment of the present invention with active right nostril odorant or pure odorant pathing.
Figure 12A:
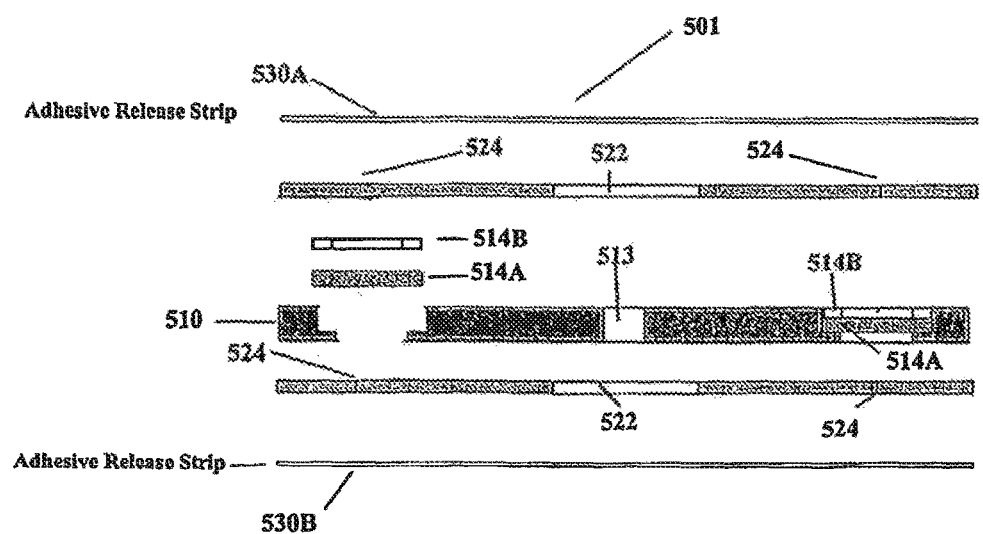
FIG. 12A illustrates a side exploded view of one embodiment of an odorant or pure odorant cartridge.

FIG. 10A illustrates one embodiment of the device 500 with active, i.e., pure odorant infused airflow, left nostril pathing and passive (no odorant infused air) pathing for the right nostril. FIG. 10B illustrates the device 500 of FIG. 10A rotated 180 degrees so that the right nostril path is active and the left nostril path is passive.

The exchangeable odorant or pure odorant cartridge or aroma media disk 501 consists of a rigid central body 510 which may be approximately the size of a standard CD Rom used with computers. The central body 510 has a hub hole 513 that is indexed to cause one pure odorant chamber 512 containing pure odorant media, e.g., an absorbent pad or pellet 514, at a time to be aligned with internal airways. The central disk has at least two chambers 512 designed to support absorbent pads or pellets 514 which may progressively be aligned with airways. The chambers 512 may be designed with an offset or air gap 516 to prevent capillary action allowing liquid aroma containing fluid to leak out of the chamber 512.

An embodiment of the cartridge 501 is illustrated in FIGS. 11A-11C and 12A-12F, including illustration of insertion of a pure odorant media 514 into a chamber 512. FIG. 12 provides a side exploded view of the materials and structure of one embodiment of the cartridge 501. On either side of the central body 510 are silicone or similar material disks 520A, 510B, adhesively attached to the central body 510. The first and second silicone disks 520A, 520B, each have a hub hole 522 in the center matching the hub hole 513 in the central body 510 and a die cut slot 524 functioning essentially as a valve that passes over the pure odorant chambers 512 such that the slot 524 passively covers all the pure odorant media therein. This slot 524 is best seen in FIG. 11A.

Thus, when air is forced against the first flexible silicone disk 520A, air is forced through the slot 524 and allowed to flow through the aroma infused pure odorant media, e.g., pad or pellet, to create pure odorant infused air which is forced through the slot 524 on the second silicone disk and into active airway whereby the aroma infused air is ducted into the active cannula to be inhaled by the test subject. When air is not passing through a given chamber 512, the silicone material returns to a passive sealing position. The silicone disks are permanently attached to the central disk trapping the absorbent pads in place.

On the outer surface of both silicone disks is a release strip 530A, 530B which covers both sides of the cartridge 501, i.e., covering the first and second silicone disks 520A, 520B and the slots 524 therein, such that they must be removed to load the cartridge 501 into the aroma presentation device body.

Figures 13A, 13B, 13C:
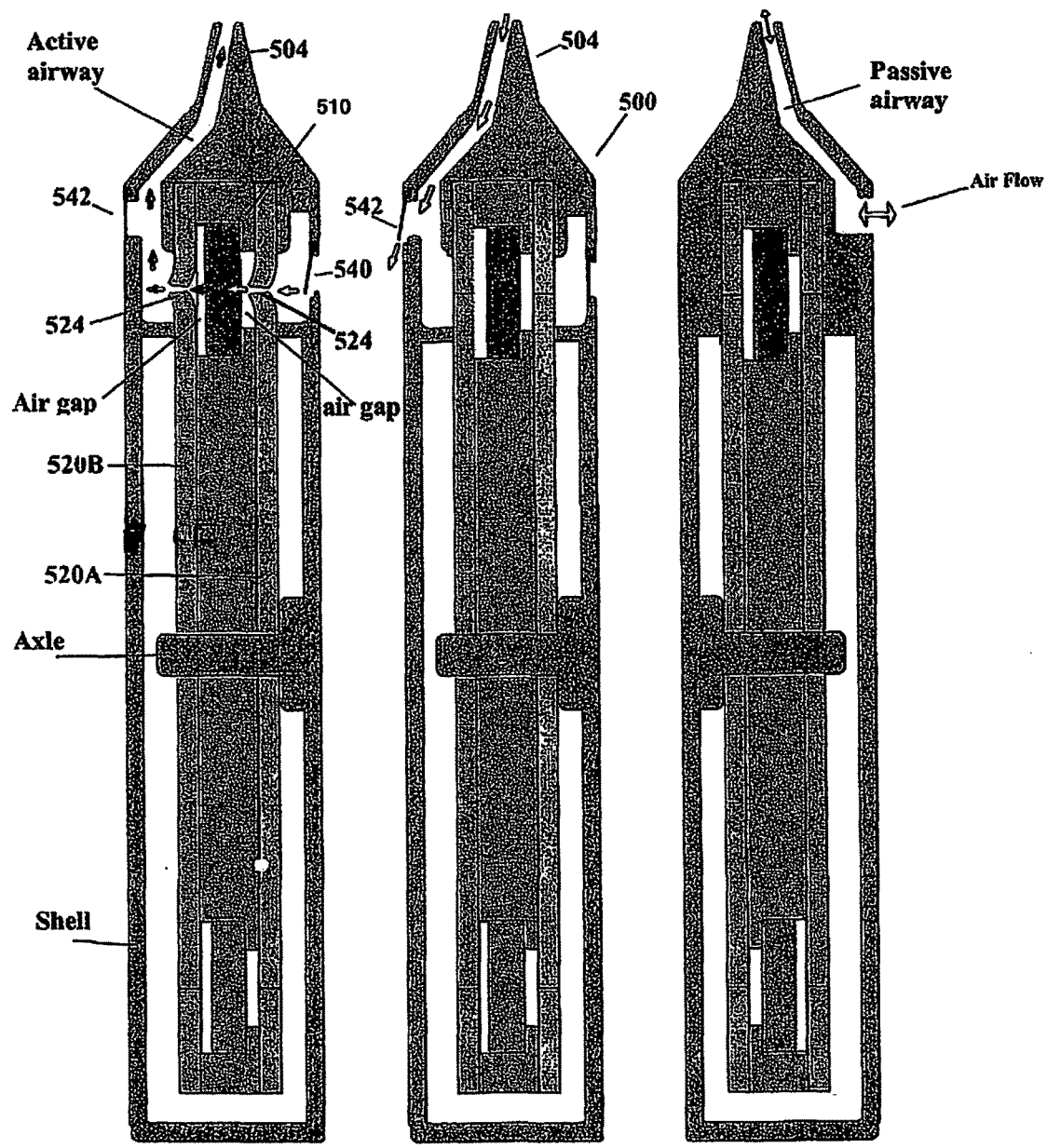
FIG. 13A illustrates a side and cross-sectional view of one embodiment of the present invention in active nostril inhalation mode.
FIG. 13B illustrates the embodiment of FIG. 13A in active nostril exhalation mode.
FIG. 13C illustrates the embodiment of FIGS. 13A and 13B in passive nostril inhalation and exhalation mode.

FIGS. 13A-13C provide illustration of the airflows in the device during operation. FIG. 13A illustrates the active nostril pathway, with atmospheric air passing through a one-way valve 540 to teach the first silicone disk 520A and slot 524 therein. The air passes into the designated and aligned odorant or pure odorant chamber, with pure odorant media therein, where the air becomes infused with the odorant or pure odorant disposed within the aligned chamber. The air flow continues as the odorant or pure odorant-infused air flows through the slot 524 in the second silicone disk 520B and upward past one-way valve 542 and through the nasal port 504 into the active first nostril. Meanwhile, the passive second nostril is in fluid communication with atmosphere as shown in FIG. 13C. Finally, the active first nostril comprises an exhalation path as in 13 B where the active first nostril exhales air into the nasal port 504 where it opens one way valve 542 and exits the device 500 to the atmosphere.

Figure 14A:
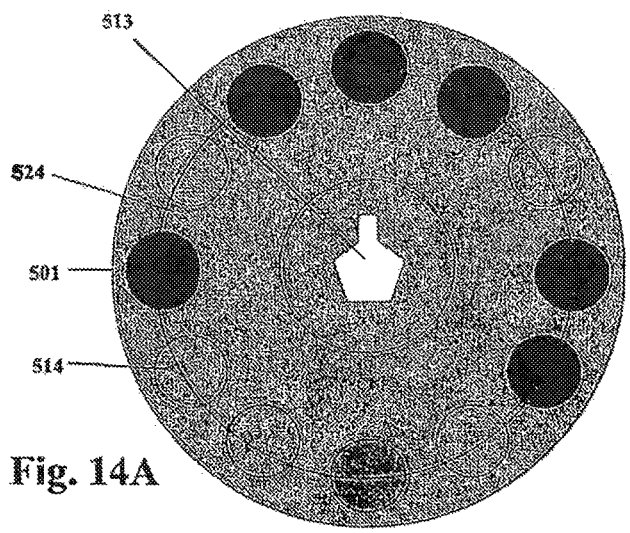
FIG. 14A illustrates a top view of one embodiment of odorant or pure odorant cartridge.
Figure 14C:
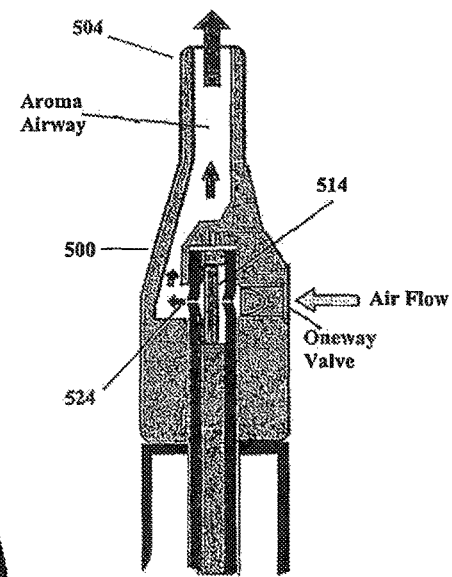
FIG. 14C illustrates a side cutaway view of one embodiment of the present invention.
Figure 14B:
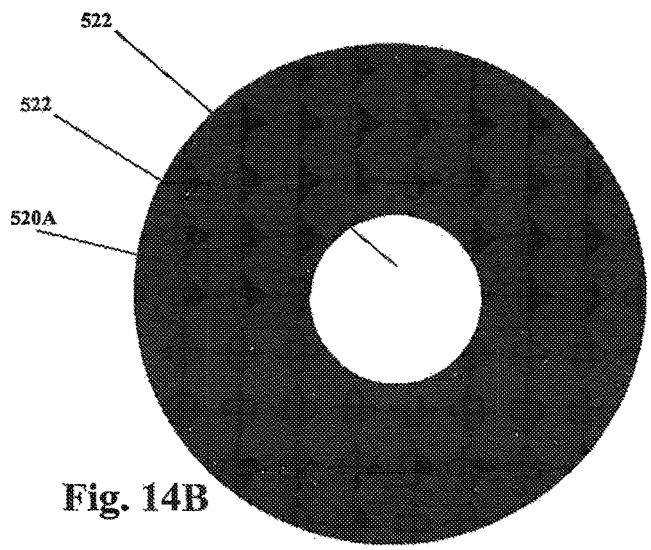
FIG. 14B illustrates a top view of a layer of material for one embodiment of the odorant or pure odorant cartridge.

FIGS. 14A-14C further illustrate the device of FIGS. 10A-13C. Thus, cartridge 501 is provided as described previously. In this embodiment, however, the hub hole 513 is non-circular. Specifically, a keyed geometry is employed for hub hole 513 to enable engagement with, e.g., the advancer mechanisms discussed supra, see, e.g., FIGS. 6A (ratcheted gears) and 6B (wound spring or clock spring) for specific examples.

Figure 15A:
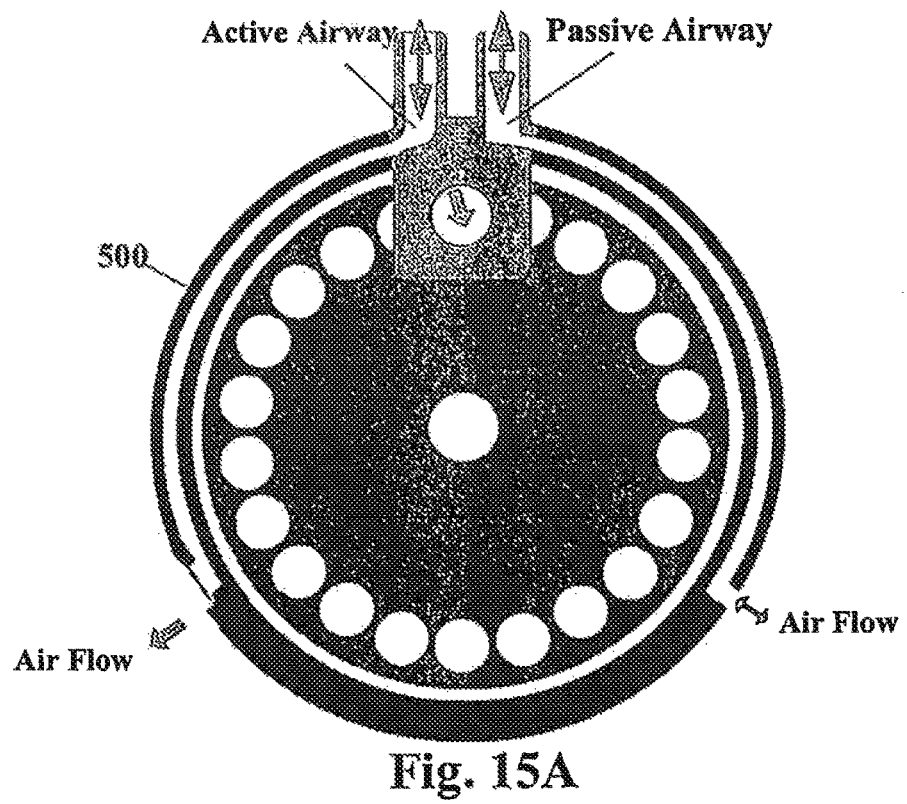
FIG. 15A illustrates a top cutaway view of one embodiment of the present invention.
Figure 15B:
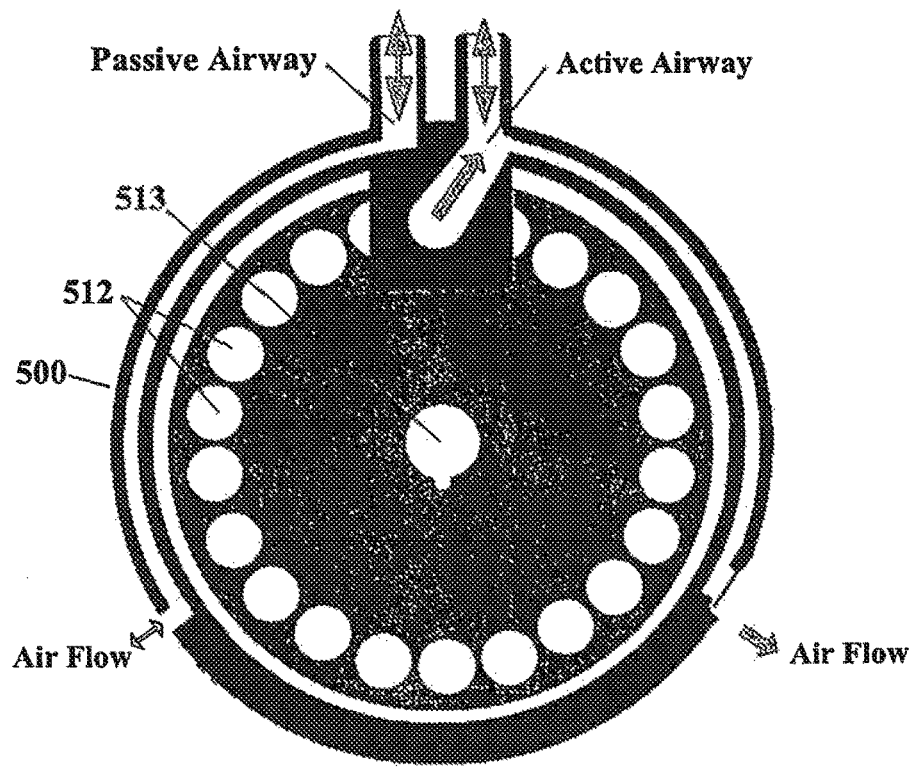
FIG. 15B illustrates a top cutaway view of one embodiment of the present invention.
Figure 16A:
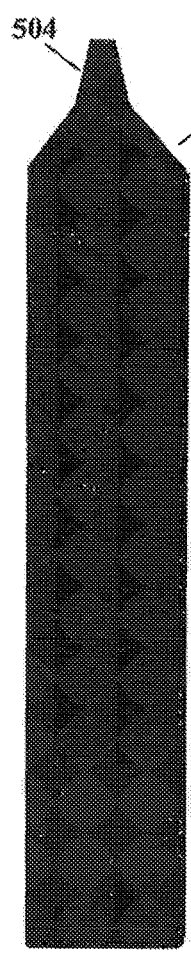
FIG. 16A illustrates a side view of one embodiment of the present invention.
Figure 16B:
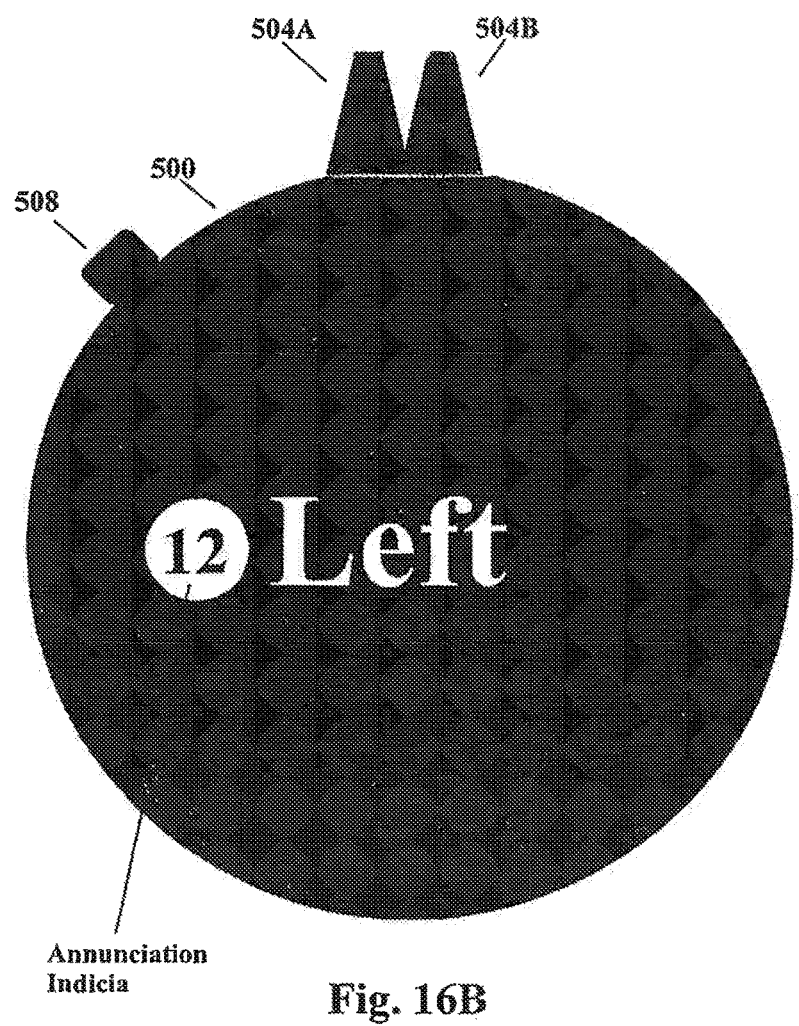
FIG. 16B illustrates a front view of one embodiment of the present invention.

Turning now to FIGS. 15A and 15B, a side cutaway view of the cartridge 501 of FIGS. 13A-13B is illustrated. Thus, the active odorant or pure odorant pathway and the passive pathway are clearly illustrated. Finally, FIGS. 16A and 16B provides a side and front view of the device 500, with advancer button 508 and rotated so that the active pathway is on the left nostril port 504B. Indication of the active pathway nostril port is provided on the front of the device as "Left". Turning the device 180 degrees provides the active pathway on the right nostril port 504A and indication of same is provided on the then-front of the device (not shown) as "Right". Further, an indexing indicia is provided with the device 500 to enable tracking of the specific odorant or pure odorant under current presentation to the patient. The exemplar in FIG. 16B indicates "12" which is associated with a specific odorant or pure odorant chamber in the cartridge 501. A key will be easily provided that matches the indexing indicia with the odorant or pure odorant currently residing within the chamber that is associated with indicia "12". Thus, each chamber will comprise a related indexing indicia which provides annunciation of the chamber under consideration and, therefore, the odorant or pure odorant, being introduced to the patient.

Note that the methods, devices and systems disclosed herein have utility for pure odorants in the measurement of bilateral pure odorant detection thresholds. These devices also may be used for any odorant, including pure or non-pure odorants. In other words, odorants that also stimulate the trigeminal nerve (non-pure) may also be used with the disclosed devices and methods.

In the case of non-pure odorants, the metric used will comprise an odorant identification threshold. Thus, the patient will be presented with the odorant-infused air as described above for pure odorant-infused air, and the next odorant sequentially introduced as soon as the patient identifies the first odorant by name. This identification point is defined herein as the odorant detection threshold. Preferably, the odorants' sequential presentation using the described devices and methods is done without a reset period between odorant introductions.

Working Example 1

In an initial study, a single nostril aroma testing device was used. The device was one liter in capacity and was used with 31 participants. The ages of those tested ranged from 15 to 84. The participants varied as to educational achievement from high school dropouts to a medical doctor. Socially the group consisted of a multimillionaire, a box boy, a high school student, several RNs and a number of retired people.

The metric of testing was cascading a set of pure odorants in an introduction sequence and counting breaths between the introduction of a fresh aroma and the participant recognizing the fresh aroma, i.e., reaching the pure odorant detection threshold. Alternatively, the time required to reach the pure odorant detection threshold may have been recorded.

The pure odorants used were applied in sequence, i.e., cascaded, without a reset period between successive introductions of the odorants and according to the following key for the randomly selected right nostril first:

R1: Lemon (Citrus family);
R2: Rose (Floral family);
R3: Spearmint (Herbal family);
R4: Cinnamon (Spice family);
R5: Clove (Spice family); and
R6: Vanilla (Spice family).

Followed by the left nostril:

L1: Lemon (Citrus family);
L2: Rose (Floral family);
L3: Spearmint (Herbal family);
L4: Cinnamon (Spice family);
L5: Clove (Spice family); and
L6: Vanilla (Spice family).

The summary data is provided in Table 1.

TABLE 1

| Patient ID | Right Nostril Total Breaths | Left Nostril Total Breaths |
|---|---|---|
| 1 | 27 | 29 |
| 2 | 16 | 13 |
| 3 | 22 | 19 |
| 4 | 27 | 20 |
| 5 | 21 | 22 |
| 6 | 28 | 21 |
| 7 | 17 | 24 |
| 8 | 24 | 22 |
| 9 | 18 | 14 |
| 10 | 18 | 21 |
| 11 | 20 | 18 |
| 12 | 19 | 34 |
| 13 | 16 | 21 |
| 14 | 20 | 19 |
| 15 | 25 | 23 |
| 16 | 35 | 25 |
| 17 | 19 | 29 |
| 18 | 17 | 18 |
| 19 | 18 | 20 |
| 20 | 17 | 14 |
| 21 | 15 | 17 |
| 22 | 18 | 20 |
| 23 | 20 | 20 |
| 24 | 26 | 36 |
| 25 | 14 | 12 |
| 26 | 18 | 18 |

Analysis:

The average number of breaths across all participants was around 4 breaths per aroma event. Those with poor lung capacity or shallow breaths tended to require 5 or 6 breaths as opposed to athletes with greater lung capacity who only required 2 breaths.

One of the participants (patient 17) was a known victim of Alzheimer's disease as confirmed by alternative means. As predicted, patient 17 had a significantly lower aroma sensitivity on the left nostril compare to the right nostril. Three participants (patients 7, 12 and 13) demonstrated a marked deficiency of the left nostril as compared to the right without any other likely cause than AD.

The remaining patients may, using this test method, be ruled out for Alzheimer's disease.

Thus, the data show that using the number of breaths required to recognize that the aroma presented has changed renders useful information formative in assessing the relative condition bilateral of the olfactory nerve. While overall scent sensitivity may be impacted, it is thought deterioration due to environmental issues such as chemical exposure are likely to affect both nostrils similarly. The thing being tested is the relative sensitivity of the nostrils not the absolute sensitivity. Some people have a stronger sense of smell than others but one side being significantly weaker only affected roughly 10% of those tested.

Using the cascading aroma method the number of breaths or seconds used as a scoring metric, required to recognize a fresh aroma is being presented are less for a strong sense of smell and more for a weaker sense of smell. Sometimes the subject would take more breaths to make sure they really did smell a fresh aroma. Those with particularly strong sensitivity were more certain the aroma was changed without more breaths.

Laboratory testing to verify assumptions behind the testing protocol can be done to satisfy scientific scrutiny. The aroma screen can be validated in a number of ways related to various metrics and methods of aroma presentation and the indirect and direct measurement of pure aroma concentration required to illicit a cognitive trigger that an aroma has been smelled in one nostril. Comparison alternative screening methods statistically validates a screening method if both consistently render a similar result.

1. A gas flow meter may be hooked up to the intake port of the device to confirm that a relativity equal rate of inhalation is used over the course of a screening.

2. The number of seconds and the number of breaths are thought to be statistically similar, but can easily be recorded together to confirm statistical similarity.

3. Counting breaths from the point in time a pure aroma was changed to the next aroma in a sequence can be validated as consistent with the concentration of pure aroma seen at the nostril with an electronic nose device in a lab.

Using the proposed rapid presentation or cascade of a plurality of pure aromas as a testing perimeter and metric also solves the problem of clearing the aroma testing device chamber and pure air pathway of a single aroma to return it to a clear air mode in preparation for the next aroma presentation testing event.

The sequential aroma cascade method simply does away with the clear air mode entirely in favor of effectively resetting the olfactory nerve by presenting a fresh aroma.

Using the plurality of sequentially presented aromas as a testing method actually simplifies the mechanical device required to present the aromas and manage the testing events. Not being required to revert to a clear air mode between testing events nullifies the need for a number of parts in many embodiments of handheld aroma testing devices.

A removable multi-chambered aroma element could be sold as a consumable test element allowing for an easy way to refresh the device. After a number of aroma tests have exhausted the rotating aroma multiple cavity cartridge, it is disposable. The replaceable cartridge contains a plurality of fresh pure aromas especially formulated at the factory to work well with the aroma presentation device. Seals covering ports in the multi cavity aroma chamber are removed and the fresh aroma cartridge is installed.

Generally speaking, contamination of the pure odorants with any additional additives or ingredients that might also excite the trigeminal system should be avoided. In addition, common commercial aroma "essential oil" bases and preservatives might tend to coat the airways of the aroma chamber and gas pathways with commercial aroma base oil materials, creating an aroma latency failure mode even where the clear air may be slightly contaminated with aroma. Thus, pure aroma materials used in the test may be better diluted with water or trace amounts of alcohol which would evaporate and not leave a latent odor on the interior surfaces of the testing device. Additionally, the lowest concentration and amount of aroma that is still detectable by the user will reduce aroma latency on the air pathways of the device. Certain coatings on the inner surfaces of the devices disclosed herein may also tend to repel the aroma molecules instead of presenting a surface to which the aroma molecules adhere. Alternatively, lining the interior of the aroma presentation device with an electrostatic mat might capture and hold aroma molecules to maintain a clear air pathway without contamination of the pure air. Such material can be washed off to recharge the electrostatic resins use in such products as furnace air filters.

A computerized application and alternative embodiment of the method may be provided. Here, the data may be entered by hand into a spreadsheet previously created and saved within the memory of a programmable computing device, accessory or appliance such as previously described or may be automatically communicated by, e.g., a USB device as described herein that is connected to the testing device and in communication, i.e., wired or wireless, with the computing device. In addition, the computing device can control the testing device in terms of stopping and starting aroma presentations.

Moreover, a software database and testing protocol support application(s) may be used to achieve the testing described herein with any of the disclosed device and system embodiments of the present invention. The software database may be within individual computing devices and/or may be housed within a central server that is interconnected with individual computing devices that are located at testing sites. As illustrated, at least one central server is provided and in communication with at least one remotely located computing device. Central server(s) may be cloud-based which may permit controlled access from any internet connected device, preferably a secure account enabled internet connection is employed.

Thus, a programmable computing device for implementing the invention may comprise: a memory, wherein the application, including programmed instructions for running the test protocol embodiments described herein is stored and for storing test results; a processor operatively connected with the memory and which executes the application and associated programmed instructions; a display that may display the application, test data results for left and for right nostril trials, trial number, a timer and the final calculated results in terms of any differential between the left and the right nostril detection thresholds, or a differential between a previous baseline or population statistical average score, and the instant test score. The display is operatively connected with the processor and memory; and a transmitter and a receiver for operatively connecting, and communicating with, the central server. In this system, the testing results may be obtained at the testing sites and added, either manually or automatically as described herein, to the computing device for storage and possible transmission of the data to the central server.

When the testing procedure is complete, the test data may be sent, either automatically or upon prompting by the user, from the computing device at the associated test site to the remote central server. Central server comprises a memory for storing the received test data from the at least one computing device and associate test site(s) and for storing an algorithm for processing and analyzing the instant test site results; a processor for executing the programmed instructions within the stored algorithm; a transmitter and a receiver operatively connected with the at least one computing device whereby two-way communication with the at least one computing device is enabled. Central server's memory further comprises a database for storing all of the test results received from the at least one computing device which may be used to develop further refined and more robust statistical conclusions regarding relevant elements of the patient's medical history and the instant test data received from the at least one computing device for an individual patient and securely transmit the calculated disease risk score based at least in in part upon global data stored within the memory of the central server and reported to the local computing device. Robust encryption and security features may be employed to protect individual patient's privacy rights.

This refinement will thus enable, e.g., a progressively more robust test result that may allow detection of a significant differential or change in the test data for an individual patient. For example, early onset of Alzheimer's disease may be detected progressively earlier as the database becomes more populated to eventually become a vast library of relevant medical history and patient test data and, as a result, becomes more robust. Thus, certain embodiments of the database of the central server may allow analysis of the data within the database for generation of the smallest possible differential in the olfactory threshold values, left vs right, that is still clinically significant. This is the point at which the device, systems and methods of the present invention will allow earliest possible detection of asymmetry and, in turn, earliest possible detection of Alzheimer's disease.

Similarly, in the case of symmetrical olfactory dysfunction, the database of the central server may be analyzed to determine the smallest change, from either baseline or from a prior test point or from a population statistical average, that may be considered clinically significant. This represents the finest analysis and diagnosis possible for symmetric olfactory dysfunction and the ability to monitor the underlying condition or disease progression and/or the efficacy of the treatment regimen.

The algorithm of the central server may analyze the data received from the at least one computing device and, when analysis is complete, the central server may transmit an electronically secure summary of the testing results as a risk score as described above back to the computing device at the test site so that the user, i.e., a health care provider, can observe the results by, for example, a secure email sent to a predetermined email address.

In addition, a separate application or, alternatively, an internet browser supported client program may supply a checklist of a patient's pre-testing history and enable establishing of the patient's clinically acceptable baseline of nasal performance, including any relevant medical history factors such as structural or medical issues that may compromise the left or the right nostril/airway performance and/or efficiency. This baseline value may be incorporated into the above algorithm to provide a corrective factor that essentially treats any observed airway performance for the left and/or right nostril and associated airway as a variable that may skew the final results if not corrected. The database described above may also accept input of this data and incorporate it into the analysis phase to enable a corrected result to be calculated and typically securely communicated to the appropriate computing device and associated test site.

As described above, certain embodiments of the disclosed devices of the present invention comprise measurement of the concentration of the odorant, or pure odorant, presented to the patient's nostrils that are required to evoke a response by the patient, i.e., an indication that the pure odorant detection threshold was reached.

Still further embodiments may capture the number of breaths a patient requires to inhale through the various devices and methods of the present invention to reach the olfactory threshold for each nostril. The breath data may be captured and analyzed for example, by the computing device application and/or at the central server(s) as described above.

A combination of data types may be obtained using the devices and methods of the present invention, e.g., capturing the elapsed time between introducing aroma to the aroma airway passage and the detection thereof by the patient, the number of breaths required to detect the introduced aroma and/or the absolute concentration of odorant, or pure odorant, required to reach the olfactory threshold for each nostril. The data may be analyzed by the local computing device's application and/or analyzed remotely at the central server(s) as described above in order to determine the patient's odorant, or pure odorant, detection threshold.

In certain embodiments, the testing protocol may be accomplished using the various devices and systems of the present invention described above by slowly increasing the concentration of aroma until the trigger point of cognitive notice is reached. This may be done by measuring the time it takes to recognize an increasing aroma level. Similarly, the number of inhalations required during a testing event required to detect the aroma may be significant, simple and useful measurable standard.

In an alternative embodiment, an absolute aroma concentration testing method, a real time digital "electronic nose" measurement of the actual parts per million of pure aroma per a known volume of breathable gas may be used. The aroma concentration is slowly increased to reach the required minimum saturation level required to trigger the pure aroma detection threshold. That digital value becomes a data point for the nostril being tested. A test event result might be based upon an average of, e.g., 0.000340 ppm on the left side and 0.000580 ppm on the right side. The ppm score can be converted to a L/R ratio such as, 0.000340/0.000580 or some other mathematical notation suitable for statistical analysis and reporting the data in a useful form to a health care provider.

Certain laboratory testing equipment is able to accurately identify and quantify a very specific aroma or exact sets of specific aromas in real time and displayed concentrations digitally in parts per million. These electronic smelling devices are well known to the skilled artisan. Electronic nose modules are thus very sensitive, but only detect a very narrow range of organic or chemical odor that they are "fingerprinted" to detect.

Using electronic nose modules in a bilateral clinical aroma detection threshold testing device is disclosed. As the concentration of a pure aroma in a breathable gas is slowly increased, a real-time digital readout slowly rises numerically, until the subject notes in cognitive recognition that an aroma is detected. The numerical readout may be automatically fixed or frozen at the level required for cognitive notice that an aroma has been detected when the test administrator removes their finger from the aroma control button.

The clinical testing personnel notes the ppm displayed which was required to elicit the reaction and also notes which nostril was being tested by that particular testing event. Data record keeping may be accomplished, as described herein, by a computer attached by USB or wire or radio system such as Bluetooth or Wi-Fi, to the testing device or testing results may be scored and calculated on paper.

Taking a clinically accepted baseline of individual nasal air flow performance into account, reduces test error and enhances the overall efficacy of the disclosed aroma test. If a person has a severely reduced airflow in one nostril, without taking that issue into account, test results might be skewed. Below are at least some of the ways to validate a clinically suitable "baseline of nasal performance".

Relative airflow measurement of the nostrils overcomes most inhalation air volume impediment variables or at least make the testing personnel visually and/or graphically aware of the issue in a quantitative way. Direct airflow testing with dual gas flown meters, visually comparing the actual inhalation volume of the two nostrils at the same time, is certainly the most important consideration for establishing a nasal performance baseline. A bilateral inhalation airflow testing device as previously disclosed has two airflow readout elements displayed side by side to visually compare the nasal inhalation performance of the two nostrils, wherein the testing and comparing is accomplished at the same time for the two nostrils.

The subject may be shown the readout in a mirror and is asked to inhale gently such that the top ball is near a mark on the readout. The ball that is constantly lower indicates that the indicated nostril has a lower airflow volume. A bleed valve might be provided to "set" the upper limits and calibrate the readout at the factory. An airflow inhalation testing device is built into some embodiments of the testing apparatus. Flow meters with a sufficient gas flow rate encompassing maximum nostril performance may also be used.

In addition to actually testing the relative airflow of the nostrils, the following items need to be considered in establishing a clinically acceptable baseline of nasal performance and the appropriateness of testing a particular patient with the disclosed devices, systems and methods.

A medical history of the patient may be obtained in regard to injury to the nose, the individual nostrils and associated airways and inhalation performance thereof, known or observed structural abnormalities, significant nose bleeds, a history of sinus infections, known strokes or T.I.A.s, current nasal congestion, a diagnosis of deviated septum, any previous nasal surgery, nasal tumors, polyups, allergies, a history of exposure to strong industrial odors, age, etc., to enhance the clinical significance of the results of the present invention and, potentially, to disqualify certain individuals from taking the test.

An illuminated optical examination of the nasal passage may be executed to identify mucous plugs, serious inflammation or other structural or medical impediments to a freely flowing nasal airway.

Administering a decongestant or other medicine to open airways may also be indicated in certain patient prior to nasal airflow measurements and aroma testing.

Retesting the subject at a later time of the same day or at later date may also mitigate temporary nasal conditions that might otherwise skew the test results.

A sliding scale, or corrective factor as described above, to mathematically adjust, or "handicap" the bilateral smelling acuity scores for a non-symmetrical baseline of nasal air flow may be applied to the aroma scale test results.

Cutoff levels will be established which will disqualify certain people from being considered a good candidate for the disclosed pure aroma detection test.

The disclosed aroma testing devices may be "tuned" in a number of ways during the industrial design process towards creating ideal efficacy as will be understood by the skilled artisan. For example, the diameter of the air intake ports, the diameter of gas supply tubes, the diameter of ports into and out of the aroma chamber, the size and diameter of the clear air chamber, the diameter of cannula tubes and disposable nasal cannula parts can be enlarged or constricted to achieve effective control of aroma concentration. Thus, time intervals or breaths may be adjusted as required to reach a threshold condition through scaling the apparatus. Electronic ultrasonic aroma emitters may also be adjusted to create a weaker or stronger aroma concentration.

The concentration of aroma may also be controlled by using various pure aroma producing materials and by controlling aroma dilution and the amount used. The surface area of the aroma chamber and surface area of the aroma source exposed to passing air are also controllable design variables. A minimum amount of aroma detectable is preferred, to reduce possible latency of aroma in what is intended to be substantially clear air. Coatings, filters and aroma absorbing elements may be applied to various embodiment to repel and/or absorb aroma molecules, thereby reducing latent aroma in what is intended to be substantially clear air.

Aroma sources as described herein may be in the form of a liquid held in an absorbent porous material such as a wick, stiff blotter slide or a cotton ball that is placed in the aroma chamber of the test apparatus. A viscous material such as peanut butter could be wiped onto a slide like element and inserted into the aroma chamber or the material supplied in a disposable portion package with removable seal top. Odorants, or pure odorants, may be used as discussed herein.

Such aroma/odorant diffusion devices are suitable to use as a cartridge that is inserted into the housing of the various devices as described herein. Such devices are refillable and may be filled with any essential oil. USB type ultrasonic devices emit little aroma when switched off. They may be used in the test devices of the present invention comprising, e.g., a single air chamber, thus reducing the complexity and parts required to manufacture such devices.

Repeating the testing protocol discussed herein a number of times, no matter which embodiment is used, with a randomized rotation between the nostrils and fully purging unscented airways between testing events, will create a meaningful and repeatably accurate and clinically acceptable test result.

As discussed above, the results from the use of the various embodiments of the devices, systems and methods of the present invention may be used to identify an asymmetry in a patient's olfactory threshold determined for the left and right airways. In the case of pure odorants used in the testing protocol, e.g., if an olfactory deficiency is detected via a higher olfactory threshold in the patient's left nostril and associated airway, this may provide early indication of Alzheimer's disease.

Alternatively, the results from the use of the various embodiments of the devices, systems and methods of the present invention may be used to identify an olfactory dysfunction, as compared with a baseline value, that is generally symmetrical as determined by the patient's olfactory threshold in the left and right airways. Once this type of dysfunction is determined, the patient's olfactory threshold may be monitored for several purposes including, but not limited to, monitoring the progress of the disease and/or condition contributing at least in part to the symmetrical olfactory dysfunction and/or monitoring the efficacy of a treatment regimen developed to treat the underlying disease, condition and/or olfactory dysfunction.

Actually diagnosing AD certainly rests with Doctors. Presenting the results of a comprehensive medical history analysis and also factoring in any specific AD screening results available, with appropriated weight being given each element of medical information, might be produced uniformly by a computerized data base system. The server would run an algorithm designed to weigh relevant data according to their efficaciousness and specificity for AD and render an AD stage assessment for local Doctors.

The disclosed algorithm concept, consists basically, of a complex database software program, factors all known risk factors and screening results, would be utilized to issue an AD risk factor. A universal risk factor scoring method would thus assist Doctors in making a clinical diagnosis more easily and much earlier in the progression of the disease. The algorithm would be continually adjusted to increase accuracy as more relevant data becomes available.

It is important for the purposes of doing clinical drug trials that groups of patients with early AD and those persons with little AD risk be identified. A large data base that contains medical histories and AD screening test results of many patients would allow computer data based observational studies to be done.

Designing and running a computerized database report, predicated upon certain aspects of the data, suspected AD risk factors could be quickly confirmed or found to be statistically irrelevant. Assume the data base has a yes or no answer to the question, "do you snore?" A researcher wants to know if breathing difficulties defined by snoring during sleep might be a risk factor for AD. Run the data and find out, in mere seconds Medical History and Screening Information items to be considered in a comprehensive AD Risk Factor Scoring System. This system would separate patient into low, medium, high and very high risk for AD categories.

The items in an AD medical history inventory are subject to change as new risk factors are suspected and previously identified potential risk factors are ruled out. Thus, the questions asked in the medical history form and the weight given each element are a dynamic that must be continuously adjusted as more data becomes available.

All AD screening tests included may be given weight based upon specific efficacy, (the occurrence of false positives and false negatives).

While a patient might have a strong risk factor based upon their medical history, an 80 year old with no amyloid plaque deposits on their retina and no deterioration of the olfactory nerve have virtually no risk of developing AD before they are statistically dead due to the period it takes for AD to fully develop.

Re-screening is still recommended however, in case AD indications arise later on. Also, such a person by eliminating AD, but who has still has some dementia is helped. Their condition must be due to some other medical reason and the Doctor needs to know that.

Ruling out AD is just as important as diagnosing it. The relief it would give people to know that they are at a very low risk for ever developing AD means a lapse in memory wouldn't cause panic, fearing that their minds are slipping away. People who have seen family members deteriorate are certainly emotionally charged regarding that risk in their own case.

A standardized AD Risk Factor System which takes all efficacious screening tests and medical history items into account to render a risk score would tend to create a more universal medical characterization of AD patient condition, furthering the medical art. A doctor who knows a certain patient has a high risk factor might order a Cur Cumin Study to rule out AD.

The proposed Risk Factor material below is far from a finished product as each risk factor is based on recent data a subject to constant revision.

Sample Medical History and AD Risk Factor questions, an example:

1. Age AD Development Risk Doubles every 5 years after 80
   80=0, 85=+10 90=+20 95=+25 100=+5
2. Sex, Female 50% greater risk than men
   M=0 F=+50
3. Do you smoke? How many packs a day? 59% risk factor
   1=+20 2=+30 3=+40
4. Blood Pressure numbers for Pulse Pressure, over 60 risk factor
   PP60=+25 PP65=+30 PP70=+40
5. Total Cholesterol,
   180=+20 190=+30 200=+40 210=+50 220=+60 225=65
6. Weight m Midlife Obesity 60% risk factor
   BMI at 40 greater than 100=+50
7. Height, Calculate current BMI
8. Family History of AD,
   No=0 Yes=+30
9. Do you Snore?
   No=0 Yes=+20
10. Been Diagnosed with Sleep apnea?
    No=0 Yes=30 Use a CPAP? Yes-10 No=0
11. Education years, Highest Grade level Achieved
    6=+50 7=+40 8=+30 9=+20 10=+10 11=0 12=−10 13=−20 14=−30 14=−50
12. How old was your mother when you were born?
    30=0 35=+20 40+=+40
13. Do you have migraine headaches?
    No=0 Yes=+40
14. Been exposed to fumigants at work, as professional pest control?
    No=0 Yes=+50
15. Have you been exposed to defoliants?
    No=0 Yes=+50
16. Ever been hospitalized for head trauma, such as a concussion?
    No=0 Yes=+40
17. Are you diabetic? Type I or Type II? 46%
    No=0 Yes=+50
18. Ever had a stroke?
    No=0 Yes=+50
19. Have you been diagnosed with heart disease?
    No=0 Yes=+50
20. Have you suffered from serious depression requiring medication? 65%
    No=0 Yes=+50
21. Have you had your DNA decoded? AD Risk Gene noted
    No=0 Yes=+100
22. Do you take low dose aspirin every day?
    No=+50 Yes=0
23. Do you take Blood thinners?
    No=+30 Yes=0
24. Women, do you take Estrogen hormone replacement
    No=0 Yes=+50
25. Are you Physically inactivity 82%
    No=0 Yes=+40
26. Midlife Hypertension 61%
    No=0 Yes=+40
27. Hearing loss documented
    No=0 Yes=+20
28. Low Cognitive Test Score
    No=0 Yes=+200

A risk factor score of 250+ Low Risk Factor

A risk factor score of 500+ is stage 2 Moderate Risk Factor

A risk factor score of 750+ is stage 3, High Risk Factor

A risk factor score of 1000+ Very High Risk Factor

Basic AD Staging Perimeters

Stage 0 in Alzheimer's Disease are those characterized as having no positive AD screen results noted. A person who has no positive screens results, despite multiple and significant risk factors may be AD free for the rest of their natural life span. For example, a person age 75 who has no amyloid plaque visualized on their retina whatsoever and has equal aroma detection ability between their nostrils is unlikely to ever develop AD or it will be so minor and so late in life that most such people would die of other causes long before serious dementia takes place. Re-screening Stage 0 patients at least every 5 years might be recommended, especially when helpful medications are finally approved.

Stage 1 in Alzheimer's Disease is characterized as the incipient stage, where dementia is not noticeable and plaque deposits on the retina are present but very limited. The aroma scale screen might show a slightly loss of aroma detection on the left side, blood tests might show a very limited amount of AD associated lipids. The lowest level of detectable characteristics of AD onset by any set of dependable screening methods broadly define Stage 1.

Stage 2 in Alzheimer's Disease is characterized as the AD development stage when significant plaque is deposited in brain and retinal tissue. The aroma scale would show a marked loss of pure aroma detection on the left side and a serious cognitive decline will be noticed by the patient and family. Low levels of AD related lipids would be noted in AD screening blood tests, PET scans would show plaque at detectable levels on the brain.

Stage 3 in Alzheimer's Disease is characterized by profound memory loss issues, very notable plaque deposits in brain and retinal tissue, significant loss of pure aroma detection on the left side would be noted and higher levels of AD related lipids would be noted in AD blood tests.

Stage 4 in Alzheimer's Disease is characterized by severely impacted memory issues, very significant plaque deposits on the brains and retinal tissue, A profound loss of pure aroma detection ability in the left side and a recent decline in aroma detection on the right side, as well. Stage 4 is the terminal stage of Alzheimer's disease.

Managing Global Testing Data

No medical testing apparatus or method has diagnostic value without a convincing amount of data to document efficacy. The combination of the disclosed handheld aroma testing mechanism and aroma testing protocol with associated data, can be well managed to have dramatic potential for many purposes.

From the medical provider's point of view, there is an internet based web site containing the most recent information on the aroma scale test, provider account registration and the practice's data for its patients behind a secure login infrastructure.

The medical provider establishes an account for their practice that includes providing a physical clinic shipping address, phone numbers, credit card account information, a designated email account and other contact information.

A password protected "provider account" is thus set up to support the online purchase of Aroma Scale devices, consumable Aroma Cartridges, nostril airflow testing meters, etc. A unique Medical Provider Account identifier code is provided which is used in establishing secure patient file access. Provider accounts include an automatic payment system utilizing a credit card for paying for aroma scale reporting services and products.

A computer application that runs on iPad, iPhone, Android, Macs and PCs allows secure patient data files to be established and the data accessed by the medical provider.

Secure Patient files contain relevant medical history, nostril airflow data and dated aroma scale test data for any patient given the aroma score screening test. This account information is "HEPPA secure" and may require the use of unique patient identifier codes that only the doctor can correlate with any particular patient. Follow up aroma testing is added to the existing patient file along with date and relevant medical history information.

The computer application may be in the form of a stand alone "App" that is distributed free, by Apple Computer Company and various Android App Stores. Alternatively, a web based HTML5 App would be available offering similar functions running on common web browsers.

To begin using the Aroma Scale screening system a provider would set up a provider account, order aroma scale testing apparatus and train nurses who will administer the test in their clinics. Training may be done by using a DVD or viewing videos posted on line.

A database populated with numerous patient files would allow for "virtual" observational clinical studies. Further medical history information may be added periodically to updated data input forms, as helpful risk factors are proposed. Requests for database analysis reports would be fulfilled by the central computer database under the control of the Aroma Score Company.

An extensive database would provide candidates for drug studies since known early onset AD and similarly situated people who are not early onset AD would be searchable by locality. The demand for highly concentrated early onset AD patients who are local and willing to participate in clinical trials is a major obstacle for the drug industry, worldwide in doing clinical trials.

Screening a Patient Includes the Protocol Elements of:

1. Opening a new online data entry form using an application or web form. The data entry form requires every block of data requested be entered before going to the following page to insure complete files.

2. A medical history page includes, the provider account identifier code, the system automatically loads the date of the test, requires an entry that encrypts a novel patient identifier code, records date of birth, sex, weight etc., including relevant known medical history, nostril airflow numbers and the Aroma Scale raw data.

3. Upon completing the patient data entry form the nurse enters "Submit" to send the new patient file over the internet to the Aroma Score central server. This completes the test and data entry portion of the Aroma Score management method.

4. Upon receiving the patient data file over an internet connection, the central server adds the disclosed information to a central data base and correlates the instant data provided with all existing data on the server.

5. The server then uses a proprietary algorithm to generate an AD risk score for that particular patient considering all the medical history and testing data amassed globally.

6. The server then charges the medical provider's credit card a processing fee for providing an AD risk score. Follow-up Aroma Scoring processing might be free for registered patients to encourage participation with the program long term.

7. The server then sends the medical provider an email that include the encrypted patient identification code, the report lists known risk factors for AD and an Aroma Scale Risk Assessment.

8. The medical provider then uses the Aroma Scale Risk Assessment to assist in making a diagnosis or decision to do more AD risk testing. The diagnosis could include, planning a follow up aroma scale screen in the future, doing alternative testing to confirm or exclude incipient AD in case of a high risk assessment. The risk assessment may completely clear the patient, for the time being.

Aroma Scale Risk Assessment Reports Might be Similar to these Examples:

RHeilMD@doctorsrock.com

Re; AromaScore Results for patient 6562GS78

Dr. Heil:

Your office submitted AromaScale AD screening history and test data for patient 6562GS78 on Jun. 5, 2014. Due to the following risk factors, we assign the highest risk factor to this patient. Further diagnostic testing is recommended with a follow up AromaScale screening in 6 months.

Patent Code: 6562GS78

Risk Factors for AD

1. Sex, Patient is female, 50% greater chance of developing AD

2. Age, patient is 83, risk doubles for AD every 5 years after age 80

3. Mild Dementia Noted, due to age and limited extent of dementia noted this may not be relevant, yet 4. Sleep Apnea, Patient reports sleep study indicating sleep apnea, moderate enhanced risk 5. Pulse Pressure High, 165/87, Pulse pressure well over 60 points, High Risk factor 6. Family History of AD, slight added risk factor due to one parent having AD at an age prior to 90

7. AromaScale Screen Results, 47 Left/33 Right, no significant bilateral air flow factor.

VERY HIGH RISK for early onset AD is predicted.

NOTE: Doctor Heil,

Due to the above noted high risk factors, further diagnostic testing is clearly recommended for this patient.

Patient should be advised to prepare for a notable decline in her cognitive condition over the next few year. Preparation might include obtaining long term health care insurance if she is not already covered. Any care givers need to be advised that her dementia symptoms may increase in the short term.

Follow up AromaScale testing is free, please participate in our clinical trial by helping us follow this patient's condition. Patient may be asked if they would be interested in being part of a clinical study testing new AD medicines. Such medicines might help them avoid further dementia.

Thank you, the AromaScale Team

Cur Cumin Stained Amyloid Plaque AD Screen/Confirmation

Another early onset AD screening method of great interest to the medical industry has been staining amyloid plaque and then visually identifying the plaque in the eye of a living person through the iris.

One particularly helpful "smart tag" is the bright yellow Indian spice Cur Cumin. Being hydrophobic, ingested or injected cur cumin molecules jump the blood brain barrier to attach to a molecularly sticky spot on Amyloid plaque deposits. Since some eye tissue, (notably the retina), is neural tissue much like the brain, deposits of plaque develop there concurrently with the brain and fortunately can be visualized without invasive procedures. While cur cumin stained plaques may be visualized with white light, UV light at around 400 nm tends to create a fluorescence effect with an orange glow that contrasts nicely with unstained retinal tissue tending to be another color of yellow. The plaque can be viewed through the iris with or without dilating the eye. Common Ophthalmology examination tools for visualizing the retina may be used. The gold standard of retinal examination is the dilated view of the retina.

Administering natural Cur Cumin and then examining the eye and not finding any amyloid plaque amounts to a quite persuasive negative screen result for incident AD. No plaque, no AD. Alternative causes for plaque on the retina or other features that might be notable may be discounted through prior examination of the eye by a qualified ophthalmologist. A baseline and cur cumin stained retinal image can tell a trained Ophthalmologist a lot.

Fundus photography is used to document abnormalities of the eye or disease progression and may be used for conditions such as macular degeneration, glaucoma, neoplasms of the retina and choroid (benign and malignant), retinal hemorrhages, ischemia, retinal detachment, choroid disturbances, and diabetic retinopathy. It may also be used for assessment of recently performed retinal laser surgery.

While research has been done using chemical derivatives of Cur Cumin to supposedly enhance the effect, shift the wavelength of light that excites or is fluoresced by certain wavelengths of light, natural cur cumin works well at around 400 nm without chemical enhancement of the spice. Light that simply contains the 400 nm light with other wavelengths as well still shows the plaque to the trained eye of a doctor of Ophthalmology.

Cur Cumin has been allowed legally in the United States as a food supplement and as a spice, used without serious contra-indications for many years. The effect of natural cur cumin seen on retinal tissue is well known.

What is lacking in using cur cumin as a screening method for finding Amyloid Plaque as a screen for early onset AD is a scoring method that quantifies the plaque deposits. Digital images of the retina may be sent via the internet and stored on servers for later examination by a qualified Doctor of Ophthalmology. A set of retinal images taken over time show a progression of the AD disease process as additional plaque is deposited.

Data show that while cur cumin taken orally stains amyloid plaque deposits on the retina, those patients without plaque deposits show no difference between a baseline retinal photograph and a series of photographs taken daily with a 800 mg dose of the staining agent cur cumin.

Some research indicates that cur cumin in the blood stream reaches a maximum in an hour after ingestion if it has an oil additive or a pepper extract added to aid in absorption by the body. The cur cumin in the blood steam jumps to the plaque and adheres to it creating the visual effect needed to identify retinal plaques.

Cur Cumin Stained Retinal Amyloid Plaque Detection and Scoring Method Amyloid plaque in the eye has been detected when such plaque is stained by an appropriate agent. The staining agent is applied topically to the exterior of the eye with some screens and are taken orally or injected into the blood screen to stain any plaque on the eye. Plaque may thus be seen both on the cornea and the retina. Of the methods above used to administer cur cumin, ingestion is the least troublesome to the patient and provides sufficient effect on retinal plaque to work well as a screening system.

Recently, methods of visualizing and identifying amyloid plaque in living patients have been demonstrated. Various cur cumin deviates and alternative stains such as Congo Red, special optical detection devices and methods of detection have been proposed.

However, a meaningful scoring method has yet to be introduced to the medical community to quantify such deposits seen in the eye. Evidence that cur cumin stained retinal plaque has in fact been detected in a patient's eye really doesn't facilitate a meaningful diagnosis, particularly as to staging without a universal method of comparison.

A retinal plaque stained screen method using orally administered naturally occurring cur cumin is particularly efficacious with certain steps taken to prevent false positives due to alternative reasons such plaque might be present.

Cur Cumin Retinal Study Protocol

A patient suspected of having early onset AD due to an aroma screen is referred by their general practitioner or neurologist to a local ophthalmologist. The local ophthalmologist observes the eye grounds and takes a detailed digital picture of the retina. The patient is then given cur cumin in tablet form to ingest and given a second appointment.

The follow-up appointment is to have their eye(s) re-examined after a period required for their body to absorb the cur cumin and have the cur cumin jump the blood brain barrier to attach to a receptive area on any retinal plaque that might be present in the eye.

At the second local Ophthalmologist appointment, the eyes are examined again and a second retinal digital photograph is taken using light and or filters including wave lengths around 400 nm (+ or −20 nm) At those wave length, natural cur cumin which has bonded to any retinal plaque has a fluorescence in a bright orange color that contrasts with unstained retinal tissue. The plaque is thus easily noticeable if present. A lack of plaque deposits is also visually apparent in detailed digital retinal digital photographs While strong UV light around 265 nm is harmful to eye tissue, light in the range that fluoresces cur cumin is not dangerous, especially at fairly low levels and for short periods of time.

The local ophthalmologist does not confirm or deny that plaque was visualized and then emails the first and second retinal photographs to a central server where a board certified ophthalmologist remotely reads the digital pictures to stage the plaque based upon a zero for no plaque to a higher scale number based upon the relative amount of plaque seen.

No plaque whatsoever seen means that AD is not in early stages and amounts to a negative screening result. Clearly, amyloid plaque, when detected is significant. Having also seen a baseline retinal photograph of the eye's condition before the cur cumin stain and considering the medical history of the patient allows the doctor to rule out alternative reasons such plaque is seen that are due to alternative conditions than AD.

The diagnosis of retinal plaque and its relative concentration is reported back to the local general practitioner or neurologist who may inform the patient, order other confirming screens or advise the patient that there is no indication of AD development at this time.

Staging AD from the retinal image is:

Stage 0, a negative result of the study, the patient is not developing AD.

Stage 1, the minimum amount of plaque detectable, this person is likely early onset for AD.

Stage 2, Plaque is clearly notable and in greater amounts than stage 1.

Stage 3, The plaque is very notable and in greater concentration than stage 3

Stage 4, the most plaque seen in such studies, this person is profoundly diseased and likely in the terminal stage 4 of AD.

The local Doctor is then advised by email sent only to a designated email address for their practice by the central screening system, as to the relative amount of retinal plaque seen and a comprehensive AD risk score.

The cur cumin testing protocol may be used as an additional AD screening tool following a positive screen using the above methods, devices and systems. Alternatively, the cur cumin testing protocol may be used as a confirmatory AD test, following a positive screen using the above methods, devices and systems.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

The invention claimed is:

1. A method for cascading at least two pure odorants to the nostrils of a patient, comprising:
    providing at least two pure odorants capable of stimulating the first cranial nerve of the patient but not the fifth cranial nerve;
    establishing an introduction order for the at least two pure odorants;
    introducing the at least two pure odorants in pure odorant-infused air in the established introduction order to the patient's first nostril, wherein the first nostril is the patient's right or left nostril, wherein when the patient indicates reaching the pure odorant detection threshold for an introduced pure odorant, the next successive pure odorant in the introduction order is introduced to the first nostril;
    measuring and recording a metric for an olfactory threshold latency period, the metric measuring the number of breaths taken by the patient between the introduction of the pure-odorant infused air to the reaching of the pure odorant detection threshold for each introduction of the pure odorant-infused air to the first nostril;
    introducing the at least two pure odorants in pure odorant-infused air in the established introduction order to the patient's second nostril, wherein when the patient indicates reaching the pure odorant detection threshold for an introduced pure odorant, the next successive pure odorant in the introduction order is introduced to the second nostril;
    measuring and recording the metric for an olfactory threshold latency period, the metric measuring the number of breaths taken by the patient between the introduction of the pure-odorant infused air to the reaching of the pure odorant detection threshold for each introduction of the pure odorant-infused air to the second nostril;
    comparing the measured and recorded metrics for the olfactory threshold latency period recorded for the left nostril with the measured and recorded metrics for the olfactory threshold period recorded for the right nostril;
    determining whether the olfactory threshold latency period measured for the left nostril statistically differs from the olfactory threshold latency period measured for the right nostril; and
    concluding that the patient's left olfactory lobe has more damage than the patient's right olfactory lobe if the olfactory threshold latency period measured for the left nostril is statistically greater than the olfactory threshold latency period measured for the right nostril.

2. The method of claim 1, wherein the measured and recorded metric for the olfactory threshold latency period further comprises the elapsed time required by the patient to reach the pure odorant detection threshold for each introduction of pure odorant-infused air in the established introduction order.

3. The method of claim 1, wherein the pure odorant detection threshold consists of the point at which the concentration of pure odorant molecules for each one of the pure odorants introduced saturate the patient's olfactory nerve to the extent that a cognitive reaction occurs in the patient.

4. The method of claim 1, further comprising each pure odorant comprising a substance that stimulates the olfactory cell receptors of the first cranial nerve and that do not stimulate the fifth cranial nerve.

5. The method of claim 1, further comprising:
    switching from presenting a first pure odorant air flow to one of the patient's nostrils upon cognitive notice of the first pure odorant by the patient indicating reaching of the pure odorant detection threshold for the first pure odorant with the nostril; and
    presenting without delay a second pure odorant air flow to the nostril, whereupon the patient's cognitive notice of the first pure odorant is replaced by cognitive notice of the second pure odorant when the pure odorant detection threshold is reached for the second pure odorant.

6. The method of claim 1, further comprising summing of each of the measured and recorded metrics for the olfactory threshold latency periods measured in the number of breaths taken by the patient for each of the left and right nostrils.

7. The method of claim 6, further comprising comparing the summed metric for the olfactory threshold latency periods for the left nostril with the summed metric for the olfactory threshold latency periods for the right nostril and determining whether the left nostril's olfactory threshold latency period statistically differs from the olfactory threshold latency period for the right nostril.

8. The method of claim 7, further comprising concluding that the patient's left olfactory lobe has more damage than the patient's right olfactory lobe if the olfactory threshold latency period for the left nostril is statistically greater than the olfactory threshold latency period for the right nostril.

9. The method of claim 7, further comprising concluding that the patient's left olfactory lobe is not damaged relative to the patient's right olfactory lobe if the olfactory threshold latency period for the left nostril is not statistically greater than the olfactory threshold latency period for the right nostril.

10. The method of claim 1, further comprising the at least two pure odorants consisting of the same pure odorant wherein the established introduction order comprises the pure odorant in successively increasing concentration until cognitive notice indicating the patient has reached the pure odorant detection threshold.

11. The method of claim 1, further comprising providing a device to introduce the at least two pure odorants in pure odorant infused-air to each of the patient's nostrils.

12. The method of claim 11, the device further comprising oleophobic airways.

13. The method of claim 11, the device comprising:
a hand-held housing defining a chamber therein in valved communication with external atmospheric air;
a nasal tip with a lumen therethrough, the lumen in fluid communication with the housing chamber;
a pure odorant cartridge comprising a substantially circular rigid body and having two sides, further comprising more than two pure odorant chambers defined by the rigid body, the more than two pure odorant chambers arranged sequentially, and the cartridge being rotatably disposed in the housing; and
a pure odorant disposed within each of the more than two sequentially arranged pure odorant chambers, wherein the sequentially arranged pure odorant chambers are successively rotatably aligned to enable a selected pure odorant chamber to move into fluid communication with the housing chamber and the nasal tip lumen.

14. The method of claim 12, wherein the more than two pure odorants comprise a single pure odorant with successively increasing concentrations disposed in successive and adjacent pure odorant chambers until cognitive notice indicating the patient has reached the pure odorant detection threshold.

15. The method of claim 13, wherein the pure odorant cartridge further comprises a slot alignable with the position of each of the two or more pure odorant chambers in succession, the slot allowing atmospheric air to pass only through the aligned pure odorant chamber to create the pure odorant-infused air for presentation to the nasal tip.

16. The method of claim 15, further comprising:
advancing the pure odorant cartridge from the presenting of pure odorant infused air of a first pure odorant disposed in a first pure odorant chamber of the pure odorant cartridge to the patient's nostril upon the patient's cognitive notice of the first pure odorant, indicating the patient has reached the pure odorant detection threshold for the nostril and the first pure odorant; and
presenting a second pure odorant infused air of a second pure odorant disposed in a second pure odorant chamber adjacent the first pure odorant chamber of the pure odorant cartridge to the patient's nostril, and without aid of a reset period interposed between presentation of the first pure odorant infused air and the presentation of the second pure odorant infused air to the patient's nostril until the patient's cognitive notice of the second pure odorant indicating the patient has reached the pure odorant detection threshold for the nostril and the second pure odorant.

17. The method of claim 15, wherein at least one chamber of the pure odorant cartridge contains no pure odorant and is, therefore blank.

18. The method of claim 17, further comprising ruling out pure odorant contamination of the device if the patient cannot smell a pure odorant when the blank chamber of the pure odorant cartridge is aligned with the patient's nostril.

19. The method of claim 11, the device further comprising a bilateral visual indication that airflow is present to ensure valid results.

20. The method of claim 7, wherein the pure odorant detection metric further comprises:
summing, for each of the patient's left and right nostrils, the measured and recorded metrics for the olfactory threshold latency periods measured in seconds elapsed required by the patient to reach cognitive notice of each of the presented pure odorants;
comparing the summed pure odorant metrics metrics comprising elapsed time for the olfactory threshold latency periods for the left nostril with the summed metrics for the olfactory threshold latency periods comprising elapsed time for the right nostril and determining whether the left nostril's summed pure odorant metric olfactory threshold latency period statistically differs from the summed pure odorant metric olfactory threshold latency period for the right nostril;
concluding that the patient's left olfactory lobe has more damage than the patient's right olfactory lobe if the summed pure odorant metrics comprising elapsed time for the olfactory threshold latency period for the left nostril is statistically greater than the summed pure odorant metrics comprising elapsed time for the olfactory threshold latency period for the right nostril; and
concluding that the patient's left olfactory lobe is not damaged relative to the patient's right olfactory lobe if the summed pure odorant metrics comprising elapsed time for the olfactory threshold latency period for the left nostril is not statistically greater than the summed pure odorant metrics comprising elapsed time for the olfactory threshold latency period for the right nostril.

21. The method of claim 20, comprising concluding that the patient's left olfactory lobe is not damaged relative to the patient's right olfactory lobe if either of the summed pure odorant metrics comprising elapsed time or breaths for the olfactory threshold latency period for the left nostril is not statistically greater than the summed pure odorant metrics comprising elapsed time or breaths for the olfactory threshold latency period for the right nostril.

22. The method of claim 20, comprising concluding that the patient's left olfactory lobe is damaged relative to the patient's right olfactory lobe if the summed pure odorant metrics comprising elapsed time for the olfactory threshold latency period for the left nostril is statistically greater than the summed pure odorant metrics comprising elapsed time for the olfactory threshold latency period for the right nostril, or if the summed pure odorant metrics comprising breaths for the olfactory threshold latency period for the left nostril is statistically greater than the summed pure odorant metrics comprising elapsed time for the olfactory threshold latency period for the right nostril.

* * * * *